(12) United States Patent
Kwon et al.

(10) Patent No.: US 11,629,331 B2
(45) Date of Patent: Apr. 18, 2023

(54) METHOD OF DIFFERENTIATION OF HUMAN INDUCED PLURIPOTENT STEM CELL TO DERMAL PAPILLA PRECURSOR CELL AND USE THEREOF

(71) Applicant: SEOUL NATIONAL UNIVERSITY R & DB FOUNDATION, Seoul (KR)

(72) Inventors: Ohsang Kwon, Seoul (KR); Bo Mi Kang, Seoul (KR); Jin Yong Kim, Seoul (KR); Yoo-Wook Kwon, Seoul (KR)

(73) Assignee: SEOUL NATIONAL UNIVERSITY R & DB FOUNDATION, Seoul (KR)

( * ) Notice: Subject to any disclaimer, the term of this patent is extended or adjusted under 35 U.S.C. 154(b) by 339 days.

(21) Appl. No.: 16/632,472

(22) PCT Filed: Jul. 18, 2018

(86) PCT No.: PCT/KR2018/008123
§ 371 (c)(1),
(2) Date: Jan. 20, 2020

(87) PCT Pub. No.: WO2019/017691
PCT Pub. Date: Jan. 24, 2019

(65) Prior Publication Data
US 2021/0171906 A1 Jun. 10, 2021

(30) Foreign Application Priority Data

Jul. 19, 2017 (KR) .................. 10-2017-0091727
Jul. 18, 2018 (KR) .................. 10-2018-0083386

(51) Int. Cl.
*C12N 5/071* (2010.01)
*A61K 35/36* (2015.01)

(52) U.S. Cl.
CPC ............ *C12N 5/0627* (2013.01); *A61K 35/36* (2013.01); *C12N 2500/25* (2013.01); *C12N 2501/115* (2013.01); *C12N 2501/155* (2013.01); *C12N 2501/727* (2013.01); *C12N 2506/45* (2013.01); *C12N 2533/52* (2013.01)

(58) Field of Classification Search
None
See application file for complete search history.

(56) References Cited

U.S. PATENT DOCUMENTS

2006/0281177 A1* 12/2006 Sieber-Blum ........ C12N 5/0623
435/368

FOREIGN PATENT DOCUMENTS

| KR | 10-2016-0145170 A | 12/2016 |
|---|---|---|
| WO | 2016/114723 A1 | 7/2016 |
| WO | 2017/070506 A1 | 4/2017 |

OTHER PUBLICATIONS

BIT 9500 Serum Substitute, STEMCELL Technologies, 6 pages, retrieved from the internet Feb. 25, 2022: https://www.stemcell.com/bit-9500-serum-substitute.html (Year: 2022).*
Curchoe et al., PLoSOne 5(11): e13890, 2010 (Year: 2010).*
Herrera et al., BMC Cell Biology 2009, 10:20, pp. 1-11 (Year: 2009).*
Kang et al., Journal of Investigative Dermatology (2012) 132, 237-239 (Year: 2012).*
Kreitzer et al., Am J Stem Cells, 2013; 2(2): 119-131 (Year: 2013).*
Pettinato et al., Scientific Reports, 4:7402, pp. 1-11, 2014 (Year: 2014).*
Song et al., Developmental Dynamics 231: 741-749, 2004 (Year: 2004).*
Veraitch et al., Scientific Reports, 7: 42777, 2017, Supplementary materials and methods, pp. 1-22 (Year: 2017).*
Gnedeva et al., "Derivation of hair-inducing cell from human pluripotent stem cells", PLOS ONE, 2015, vol. 10, No. 1, e0116892, pp. 1-14.
Inamatsu et al., "Embryonic dermal condensation and adult dermal papilla induce hair follicles in adult glabrous epidermis through different mechanisms", Development, Growth & Differentiation, 2006, vol. 48, pp. 73-86.
Kim et al., "Human hair follicle regeneration with trichogenic human dermal papilla precursor cells derived from induced pluripotent stem cells", 76th Annual Meeting Portland Oregon of Society for Investigative Dermatology, Apr. 27, 2017, Abstract #857.
Veraitch et al., "Induction of hair follicle dermal papilla cell properties in human induced pluripotent stem cell-derived multipotent LNGFR(+)THY-1(+) mesenchymal cells", Scientific Reports, 2017, vol. 7, 42777, pp. 1-13.

* cited by examiner

*Primary Examiner* — Evelyn Y Pyla
(74) *Attorney, Agent, or Firm* — Vorys, Sater, Seymour and Pease LLP; Mih Suhn Koh

(57) ABSTRACT

Provided is a medium composition for differentiation of a human induced pluripotent stem cell to a dermal papilla precursor cell, a differentiation method, and a use for inducing hair follicle neogenesis using the differentiated dermal papilla precursor cell. Further provided is a method for differentiating a human induced pluripotent stem cell into a dermal papilla precursor cell having hair follicle forming ability and a composition of a dermal papilla precursor cell specific differentiation medium for the above differentiation, and have effectively induced hair follicle neogenesis consisting only of human cells without conventional mouse-human hybrid hair follicles by using the human induced dermal papilla precursor cell and a human induced epidermal precursor cell obtained through the differentiation method. Human hair follicle tissue produced is expected to be useful as a therapeutic method for patients suffering from hair loss by overcoming the limitations of hair loss treatments.

15 Claims, 24 Drawing Sheets

Specification includes a Sequence Listing.

SEQUENCE LISTING

<160> NUMBER OF SEQ ID NOS: 46

<210> SEQ ID NO 1
<211> LENGTH: 20
<212> TYPE: DNA
<213> ORGANISM: Artificial Sequence
<220> FEATURE:
<223> OTHER INFORMATION: SDC1_Specific_Forward

<400> SEQUENCE: 1
ctctgtgcct tcgtctttcc                    20

<210> SEQ ID NO 2
<211> LENGTH: 20
<212> TYPE: DNA
<213> ORGANISM: Artificial Sequence
<220> FEATURE:
<223> OTHER INFORMATION: SDC1_Specific_Reverse

<400> SEQUENCE: 2
ccaccttcct ttgccattta                    20

<210> SEQ ID NO 3
<211> LENGTH: 20
<212> TYPE: DNA
<213> ORGANISM: Artificial Sequence
<220> FEATURE:
<223> OTHER INFORMATION: BGN_Specific_Forward

<400> SEQUENCE: 3
gtctatctgc actccaacaa                    20

<210> SEQ ID NO 4
<211> LENGTH: 20
<212> TYPE: DNA
<213> ORGANISM: Artificial Sequence

```
<220> FEATURE:
<223> OTHER INFORMATION: BGN_Specific_Reverse

<400> SEQUENCE: 4
tggatggcca ggcggtcagt                                               20

<210> SEQ ID NO 5
<211> LENGTH: 16
<212> TYPE: DNA
<213> ORGANISM: Artificial Sequence
<220> FEATURE:
<223> OTHER INFORMATION: BMP4_Specific_Forward

<400> SEQUENCE: 5
gcccgcagcc tagcaa                                                   16

<210> SEQ ID NO 6
<211> LENGTH: 21
<212> TYPE: DNA
<213> ORGANISM: Artificial Sequence
<220> FEATURE:
<223> OTHER INFORMATION: BMP4_Specific_Reverse

<400> SEQUENCE: 6
cggtaaagat cccgcatgta g                                             21

<210> SEQ ID NO 7
<211> LENGTH: 15
<212> TYPE: DNA
<213> ORGANISM: Artificial Sequence
<220> FEATURE:
<223> OTHER INFORMATION: HEY1_Specific_Forward

<400> SEQUENCE: 7
gcgcacgccc ttgct                                                    15

<210> SEQ ID NO 8
<211> LENGTH: 17
<212> TYPE: DNA
<213> ORGANISM: Artificial Sequence
<220> FEATURE:
<223> OTHER INFORMATION: HEY1_Specific_Reverse

<400> SEQUENCE: 8
gccaggcatt cccgaaa                                                  17

<210> SEQ ID NO 9
<211> LENGTH: 20
<212> TYPE: DNA
<213> ORGANISM: Artificial Sequence
<220> FEATURE:
<223> OTHER INFORMATION: WIF1_Specific_Forward

<400> SEQUENCE: 9
tggcatggaa gacactgcaa                                               20

<210> SEQ ID NO 10
<211> LENGTH: 19
<212> TYPE: DNA
<213> ORGANISM: Artificial Sequence
<220> FEATURE:
<223> OTHER INFORMATION: WIF1_Specific_Reverse

<400> SEQUENCE: 10
ggcctcaggg catgtatga                                                19
```

```
<210> SEQ ID NO 11
<211> LENGTH: 20
<212> TYPE: DNA
<213> ORGANISM: Artificial Sequence
<220> FEATURE:
<223> OTHER INFORMATION: WNT5A_Specific_Forward

<400> SEQUENCE: 11
agggctccta cgagagtgct                                              20

<210> SEQ ID NO 12
<211> LENGTH: 18
<212> TYPE: DNA
<213> ORGANISM: Artificial Sequence
<220> FEATURE:
<223> OTHER INFORMATION: WNT5A_Specific_Reverse

<400> SEQUENCE: 12 gacacccat ggcacttg                                                 18

<210> SEQ ID NO 13
<211> LENGTH: 24
<212> TYPE: DNA
<213> ORGANISM: Artificial Sequence
<220> FEATURE:
<223> OTHER INFORMATION: OCT3/4_Specific_Forward

<400> SEQUENCE: 13
gacaggggga ggggaggagc tagg                                         24

<210> SEQ ID NO 14
<211> LENGTH: 26
<212> TYPE: DNA
<213> ORGANISM: Artificial Sequence
<220> FEATURE:
<223> OTHER INFORMATION: OCT3/4_Specific_Reverse

<400> SEQUENCE: 14
cttccctcca accagttgcc ccaaac                                       26

<210> SEQ ID NO 15
<211> LENGTH: 19
<212> TYPE: DNA
<213> ORGANISM: Artificial Sequence
<220> FEATURE:
<223> OTHER INFORMATION: NANOG_Specific_Forward

<400> SEQUENCE: 15
cctgtgattt gtgggcctg                                               19

<210> SEQ ID NO 16
<211> LENGTH: 21
<212> TYPE: DNA
<213> ORGANISM: Artificial Sequence
<220> FEATURE:
<223> OTHER INFORMATION: NANOG_Specific_Reverse

<400> SEQUENCE: 16
gacagtctcc gtgtgaggca t                                            21

<210> SEQ ID NO 17
<211> LENGTH: 21
<212> TYPE: DNA
<213> ORGANISM: Artificial Sequence
<220> FEATURE:
<223> OTHER INFORMATION: p75NTR_Specific_Forward
```

<400> SEQUENCE: 17
ccccctcctc ccacactgct a                                          21

<210> SEQ ID NO 18
<211> LENGTH: 20
<212> TYPE: DNA
<213> ORGANISM: Artificial Sequence
<220> FEATURE:
<223> OTHER INFORMATION: p75NTR_Specific_Reverse

<400> SEQUENCE: 18
aaccccaaac ctgactccat                                            20

<210> SEQ ID NO 19
<211> LENGTH: 20
<212> TYPE: DNA
<213> ORGANISM: Artificial Sequence
<220> FEATURE:
<223> OTHER INFORMATION: HNK1_Specific_Forward

<400> SEQUENCE: 19
gcaagaaggg cttcactgac                                            20

<210> SEQ ID NO 20
<211> LENGTH: 20
<212> TYPE: DNA
<213> ORGANISM: Artificial Sequence
<220> FEATURE:
<223> OTHER INFORMATION: HNK1_Specific_Reverse

<400> SEQUENCE: 20
gcccccagaa tagaaaggag                                            20

<210> SEQ ID NO 21
<211> LENGTH: 20
<212> TYPE: DNA
<213> ORGANISM: Artificial Sequence
<220> FEATURE:
<223> OTHER INFORMATION: SOX10_Specific_Forward

<400> SEQUENCE: 21
agcccaggtg aagacagaga                                            20

<210> SEQ ID NO 22
<211> LENGTH: 20
<212> TYPE: DNA
<213> ORGANISM: Artificial Sequence
<220> FEATURE:
<223> OTHER INFORMATION: SOX10_Specific_Reverse

<400> SEQUENCE: 22
aggagaaggc cgagtagagg                                            20

<210> SEQ ID NO 23
<211> LENGTH: 20
<212> TYPE: DNA
<213> ORGANISM: Artificial Sequence
<220> FEATURE:
<223> OTHER INFORMATION: ALX3_Specific_Forward

<400> SEQUENCE: 23
gaatgagctg cccacctctt                                            20

<210> SEQ ID NO 24

```
<211> LENGTH: 20
<212> TYPE: DNA
<213> ORGANISM: Artificial Sequence
<220> FEATURE:
<223> OTHER INFORMATION: ALX3_Specific_Reverse

<400> SEQUENCE: 24
cctgtaacgt gttccctgct                                             20

<210> SEQ ID NO 25
<211> LENGTH: 20
<212> TYPE: DNA
<213> ORGANISM: Artificial Sequence
<220> FEATURE:
<223> OTHER INFORMATION: CTNNB1_Specific_Forward

<400> SEQUENCE: 25
ctgccatctg tgctcttcgt                                             20

<210> SEQ ID NO 26
<211> LENGTH: 20
<212> TYPE: DNA
<213> ORGANISM: Artificial Sequence
<220> FEATURE:
<223> OTHER INFORMATION: CTNNB1_Specific_Reverse

<400> SEQUENCE: 26
cagtgggatg gtgggtgtaa                                             20

<210> SEQ ID NO 27
<211> LENGTH: 16
<212> TYPE: DNA
<213> ORGANISM: Artificial Sequence
<220> FEATURE:
<223> OTHER INFORMATION: SOX2_Specific_Forward

<400> SEQUENCE: 27
tgcgagcgct gcacat                                                 16

<210> SEQ ID NO 28
<211> LENGTH: 23
<212> TYPE: DNA
<213> ORGANISM: Artificial Sequence
<220> FEATURE:
<223> OTHER INFORMATION: SOX2_Specific_Reverse

<400> SEQUENCE: 28
ttcttcatga gcgtcttggt ttt                                         23

<210> SEQ ID NO 29
<211> LENGTH: 22
<212> TYPE: DNA
<213> ORGANISM: Artificial Sequence
<220> FEATURE:
<223> OTHER INFORMATION: LEF1_Specific_Forward

<400> SEQUENCE: 29
attccgggta cataatgatg cc                                          22

<210> SEQ ID NO 30
<211> LENGTH: 21
<212> TYPE: DNA
<213> ORGANISM: Artificial Sequence
<220> FEATURE:
<223> OTHER INFORMATION: LEF1_Specific_Reverse
```

```
<400> SEQUENCE: 30
gagaaaagtg ctcgtcactg t                                              21

<210> SEQ ID NO 31
<211> LENGTH: 20
<212> TYPE: DNA
<213> ORGANISM: Artificial Sequence
<220> FEATURE:
<223> OTHER INFORMATION: VCAN_Specific_Forward

<400> SEQUENCE: 31
tgttcctccc actacccttg                                                20

<210> SEQ ID NO 32
<211> LENGTH: 20
<212> TYPE: DNA
<213> ORGANISM: Artificial Sequence
<220> FEATURE:
<223> OTHER INFORMATION: VCAN_Specific_Reverse

<400> SEQUENCE: 32
cttccacagt gggtggtctt                                                20

<210> SEQ ID NO 33
<211> LENGTH: 20
<212> TYPE: DNA
<213> ORGANISM: Artificial Sequence
<220> FEATURE:
<223> OTHER INFORMATION: NOG_Specific_Forward

<400> SEQUENCE: 33
cctcatcgaa cacccagacc                                                20

<210> SEQ ID NO 34
<211> LENGTH: 20
<212> TYPE: DNA
<213> ORGANISM: Artificial Sequence
<220> FEATURE:
<223> OTHER INFORMATION: NOG_Specific_Reverse

<400> SEQUENCE: 34
catgaagcct gggtcgtagt                                                20

<210> SEQ ID NO 35
<211> LENGTH: 20
<212> TYPE: DNA
<213> ORGANISM: Artificial Sequence
<220> FEATURE:
<223> OTHER INFORMATION: GAPDH_Specific_Forward

<400> SEQUENCE: 35
attgttgcca tcaatgaccc                                                20

<210> SEQ ID NO 36
<211> LENGTH: 20
<212> TYPE: DNA
<213> ORGANISM: Artificial Sequence
<220> FEATURE:
<223> OTHER INFORMATION: GAPDH_Specific_Reverse

<400> SEQUENCE: 36
agtagaggca gggatgatgt                                                20

<210> SEQ ID NO 37
```

<211> LENGTH: 20
<212> TYPE: DNA
<213> ORGANISM: Artificial Sequence
<220> FEATURE:
<223> OTHER INFORMATION: OCT4 (endo)_Specific_Forward

<400> SEQUENCE: 37
cctcacttca ctgcactgta                                       20

<210> SEQ ID NO 38
<211> LENGTH: 20
<212> TYPE: DNA
<213> ORGANISM: Artificial Sequence
<220> FEATURE:
<223> OTHER INFORMATION: OCT4 (endo)_Specific_Reverse

<400> SEQUENCE: 38
caggttttct ttccctagct                                       20

<210> SEQ ID NO 39
<211> LENGTH: 19
<212> TYPE: DNA
<213> ORGANISM: Artificial Sequence
<220> FEATURE:
<223> OTHER INFORMATION: SOX2 (endo)_Specific_Forward

<400> SEQUENCE: 39
cccagcagac ttcacatgt                                        19

<210> SEQ ID NO 40
<211> LENGTH: 20
<212> TYPE: DNA
<213> ORGANISM: Artificial Sequence
<220> FEATURE:
<223> OTHER INFORMATION: SOX2 (endo)_Specific_Reverse

<400> SEQUENCE: 40
cctcccattt ccctcgtttt                                       20

<210> SEQ ID NO 41
<211> LENGTH: 20
<212> TYPE: DNA
<213> ORGANISM: Artificial Sequence
<220> FEATURE:
<223> OTHER INFORMATION: NANOG (endo)_Specific_Forward

<400> SEQUENCE: 41
tgaacctcag ctacaaacag                                       20

<210> SEQ ID NO 42
<211> LENGTH: 20
<212> TYPE: DNA
<213> ORGANISM: Artificial Sequence
<220> FEATURE:
<223> OTHER INFORMATION: NANOG (endo)_Specific_Reverse

<400> SEQUENCE: 42
tggtggtagg aagagtaaag                                       20

<210> SEQ ID NO 43
<211> LENGTH: 20
<212> TYPE: DNA
<213> ORGANISM: Artificial Sequence
<220> FEATURE:
<223> OTHER INFORMATION: REX1_Specific_Forward

```
<400> SEQUENCE: 43
tcgctgagct gaaacaaatg                                                 20

<210> SEQ ID NO 44
<211> LENGTH: 20
<212> TYPE: DNA
<213> ORGANISM: Artificial Sequence
<220> FEATURE:
<223> OTHER INFORMATION: REX1_Specific_Reverse

<400> SEQUENCE: 44
cccttcttga aggtttacac                                                 20

<210> SEQ ID NO 45
<211> LENGTH: 20
<212> TYPE: DNA
<213> ORGANISM: Artificial Sequence
<220> FEATURE:
<223> OTHER INFORMATION: TERT_Specific_Forward

<400> SEQUENCE: 45
tgtgcaccaa catctacaag                                                 20

<210> SEQ ID NO 46
<211> LENGTH: 20
<212> TYPE: DNA
<213> ORGANISM: Artificial Sequence
<220> FEATURE:
<223> OTHER INFORMATION: TERT_Specific_Reverse

<400> SEQUENCE: 46
gcgttcttgg ctttcaggat                                                 20
```

METHOD OF DIFFERENTIATION OF HUMAN INDUCED PLURIPOTENT STEM CELL TO DERMAL PAPILLA PRECURSOR CELL AND USE THEREOF

CROSS-REFERENCE TO RELATED APPLICATIONS

This application is a 371 of PCT/KR2018/008123, filed Jul. 18, 2018, which claims the benefit of priority from Korean Patent Application Nos. 10-2017-0091727, filed Jul. 19, 2017 and 10-2018-0083386, filed Jul. 18, 2018, the contents of each of which are incorporated herein by reference in its entirety.

SEQUENCE LISTING

The Sequence Listing submitted in text format (.txt) filed on Jan. 20, 2023, named "SequenceListing.txt", created on Jan. 20, 2023 (7.55 KB), is incorporated herein by reference.

TECHNICAL FIELD

The present invention relates to a medium composition for differentiation of dermal papilla precursor cells from human pluripotent stem cells, a differentiation method using the composition, and a use of dermal papilla precursor cells differentiated using the method for inducing hair follicle neogenesis.

BACKGROUND ART

For the treatment of permanent hair loss, hair transplantation may be considered by taking existing healthy hair that should be used as a donor for hair transplantation from patients themselves. However, patients with intractable permanent hair loss do not have a sufficient number of available hair follicles, so patients with male hair loss or childhood cancer survivors have a limitation in autologous hair follicle transplantation. Therefore, techniques for culturing dermal papilla cells (DPCs) and epithelial cells of patients having hair follicle-forming ability and using the same for hair follicle neogenesis have been proposed as a feasible treatment for a long period of time. Although several studies have reported that mouse dermal papilla cells have hair follicle-forming ability, human dermal papilla cells have a limitation in that, when cultured in vitro, the cells rapidly lose hair follicle-forming ability, and thus cannot be used to induce hair follicle neogenesis. Therefore, many studies have been attempted to improve the hair follicle-forming ability of human dermal papilla cells, but there have been no successful cases of inducing human hair follicle neogenesis using dermal papilla cells.

The hair follicle-forming ability of human dermal papilla cells or dermal papilla-like cells (DPLCs) has been demonstrated through studies on combination thereof with mouse neonatal epidermal cells to produce mouse-human hybrid hair follicles (Gnedeva et al., PLoS One 10, e0116892, 2015). However, there have been no reports of human hair follicles being newly formed using only human cells without using human neonatal tissue. Therefore, the generation of early embryo-like dermal papilla cells by direct reprogramming from pluripotent stem cells including induced pluripotent stem cells (iPSCs) or adult cells has been proposed as a potential strategy for obtaining a large number of highly induced dermal papilla cells. However, due to an inadequate understanding of the biological conditions of human dermal papilla cell lines, there is no clear protocol for differentiating into dermal papilla cells having hair follicle forming ability. In addition, there have been recent studies on the differentiation of epithelial stem cells required for hair follicle neogenesis from human pluripotent stem cells, but techniques for differentiation of dermal papilla cells required for hair follicle neogenesis together with epithelial cells from human pluripotent stem cells including human dedifferentiated pluripotent stem cells have not yet been established.

Meanwhile, dermal papilla precursor cells (DPPCs) observed in the dermis during the follicular placode phase in an embryonic development stage are known to exchange signals with epithelial placode cells at the beginning of embryonic hair follicle development. The first signal from the skin acts on the unspecified epidermis to form morphologically recognizable hair placodes, and the stabilized epidermal placode signals to the lower dermal cells to collect dermal papilla cells, thereby promoting the formation of dermal condensates. Finally, the dermal papilla precursor cells are known to send signals to the epidermis to stimulate the proliferation and downgrowth of hair germ. After hair follicle formation is completed, dermal papilla precursor cells become mature dermal papilla cells in the bulb region and become adjoining dermal sheath adjacent to mature hair follicles. Therefore, obtaining dermal papilla precursor cells with hair follicle-forming ability as in embryos is an important process for human hair follicle production. However, relatively little is known about human dermal papilla precursor cells at the time of in vivo hair follicle placode.

DESCRIPTION OF EMBODIMENTS

Technical Problem

As a result of having conducted intensive studies to address the above-described conventional problems, the inventors of the present invention developed a medium composition for specific differentiation from human pluripotent stem cells into dermal papilla precursor cells and established a differentiation method using the same, and developed a technique for inducing the neogenesis of hair follicles consisting of only complete human cells, not hybrids, using human dermal papilla cells differentiated using the above method and epithelial stem cells differentiated from human pluripotent stem cells, and thus completed the present invention.

Therefore, it is an object of the present invention to provide a medium composition for differentiation of dermal papilla precursor cells from human pluripotent stem cells.

It is another object of the present invention is to provide a method of differentiating dermal papilla precursor cells from human pluripotent stem cells and dermal papilla precursor cells differentiated using the method.

It is another object of the present invention is to provide a composition for inducing hair follicle neogenesis including dermal papilla precursor cells and epithelial stem cells as active ingredients, a method of inducing hair follicle neogenesis by delivering the composition to an individual, and a use of the composition for hair follicle neogenesis.

It is another object of the present invention to provide a method of producing hair follicles by co-culturing dermal papilla precursor cells and epithelial stem cells.

It is another object of the present invention is to provide a cell therapeutic agent for treating hair loss including dermal papilla precursor cells and epithelial stem cells as active ingredients.

However, technical problems to be solved by the present invention are not limited to the above-described technical problems, and other unmentioned technical problems will become apparent from the following description to those of ordinary skill in the art.

Technical Solution

According to an aspect of the present disclosure, there is provided a medium composition for differentiation of dermal papilla precursor cells from human pluripotent stem cells, including, in Dulbecco's Modified Eagle's Medium/Nutrient Mixture F-12 (DMEM/F12) GLUTAMAX™ (L-alanyl-L-glutamine) (Reference 1) medium, fibroblast growth factor-2 (FGF2), a glycogen synthase kinase-3 (GSK-3) inhibitor, and bone morphogenetic protein 4 (BMP4).

In one embodiment of the present invention, the GSK-3 inhibitor may be one or more selected from the group consisting of 6-bromoindirubin-3'-oxime (BIO), CHIR-99021, and SB-216763.

In one embodiment of the present invention, the FGF2 may be included at a concentration of 5 ng/ml to 30 ng/ml, the GSK-3 inhibitor may be included at a concentration of 0.1 µM to 10 µM, and the BMP4 may be included at a concentration of 0.5 ng/ml to 5 ng/ml.

In one embodiment of the present invention, the BIO may be included at a concentration of 0.5 µM to 5 µM, or the CHIR 99021 may be included at a concentration of 0.1 µM to 10 µM.

In one embodiment of the present invention, the medium composition for differentiation into dermal papilla precursor cells may consist of a Dulbecco's Modified Eagle's Medium/Nutrient Mixture F-12 (DMEM/F12) GLUTAMAX™ (L-alanyl-L-glutamine) (Reference 1) medium supplemented with fetal bovine serum (FBS), an antibiotic, fibroblast growth factor-2 (FGF2), a GSK-3 inhibitor, and bone morphogenetic protein 4 (BMP4).

In one embodiment of the present invention, human neonatal fetal tissue may not be incorporated into the medium composition for differentiation.

In one embodiment of the present invention, the human pluripotent stem cells may be human embryonic stem cells (ESCs) or human dedifferentiated pluripotent stem cells.

The present invention also provides a method of differentiating dermal papilla precursor cells from human pluripotent stem cells, including the following processes:

(a) culturing embryonic bodies of human pluripotent stem cells in a neural crest stem cell induction medium to differentiate into neural crest stem cells; and (b) culturing the differentiated neural crest stem cells in the medium composition for differentiation to differentiate into dermal papilla precursor cells.

In another embodiment of the present invention, the method may further include the following process:

(c) aging the differentiated dermal papilla precursor cells to obtain spherical dermal papilla precursor cells.

In one embodiment of the present invention, the neural crest stem cell induction medium may be DMEM/F12 GLUTAMAX™ (L-alanyl-L-glutamine) (Reference 1) medium containing fibroblast growth factor-2 (FGF2), fibronectin, insulin, $N_2$ supplement, and transferrin.

In another embodiment of the present invention, process (c) may be performed by culturing the differentiated dermal papilla precursor cells in DMEM/F12 GLUTAMAX™ (L-alanyl-L-glutamine) (Reference 1) medium supplemented with FGF2 alone.

In one embodiment of the present invention, process (a) may be performed for 5 days to 9 days, process (b) may be performed for 11 days to 17 days, and process (c) may be performed for 7 days to 13 days.

In one embodiment of the present invention, the method of differentiating dermal papilla precursor cells from human pluripotent stem cells may be performed for 26 days to 50 days.

The present invention also provides human dermal papilla precursor cells differentiated from human pluripotent stem cells by using the above-described differentiation method, wherein the human dermal papilla precursor cells have hair follicle-forming ability.

In one embodiment of the present invention, the dermal papilla precursor cells may exhibit one or more characteristics selected from the group consisting of the following (a), (b), and (c).

(a) positive immunological characteristics for alkaline phosphatase (ALP), α-smooth muscle actin (αSMA), versican (VCAN), and nestin;

(b) structural properties of dermal papilla cells that spontaneously form spheres; and (c) genetic characteristics expressing one or more dermal papilla signature genes selected from the group consisting of ALX Homeobox 3 (ALX3), SRY-Box 2 (SOX2), Hes Related Family BHLH Transcription Factor With YRPW Motif 1 (HEY1), Bone Morphogenetic Protein 4 (BMP4), Lymphoid Enhancer Binding Factor 1 (LEF1), WNT inhibitory factor 1 (WIF1), and Versican (VCAN).

In one embodiment of the present invention, the dermal papilla precursor cells may be CD133(−).

The present invention also provides subcultured human dermal papilla precursor cells differentiated from the human pluripotent stem cells using the differentiation method and having hair follicle forming ability.

The present invention also provides a composition for inducing hair follicle neogenesis including, as active ingredients, epithelial stem cells differentiated from human pluripotent stem cells and the human dermal papilla precursor cells differentiated from human pluripotent stem cells and having hair follicle-forming ability.

The present invention also provides a method of inducing human hair follicle neogenesis by delivering, to an individual, epithelial stem cells differentiated from human pluripotent stem cells and the human dermal papilla precursor cells differentiated from human pluripotent stem cells and having hair follicle-forming ability.

The present invention also provides a method of inducing human hair follicle neogenesis by transplanting, to tissue except for human, epithelial stem cells differentiated from human pluripotent stem cells and the human dermal papilla precursor cells differentiated from human pluripotent stem cells and having hair follicle-forming ability.

The present invention also provides a method of producing human hair follicles by co-culturing the human dermal papilla precursor cells differentiated from human pluripotent stem cells and having hair follicle forming ability and epithelial stem cells differentiated from human pluripotent stem cells.

The present invention also provides a use of a composition for human hair follicle neogenesis, the composition including epithelial stem cells differentiated from human pluripotent stem cells and the human dermal papilla precursor cells differentiated from human pluripotent stem cells and having hair follicle forming ability.

The present invention also provides a cell therapeutic agent for treating hair loss, including, as active ingredients, epithelial stem cells differentiated from human pluripotent stem cells and the human dermal papilla precursor cells differentiated from human pluripotent stem cells and having hair follicle-forming ability.

The present invention also provides a method of treating hair loss, including administering, to an individual, a cell therapeutic agent including, as active ingredients, epithelial stem cells differentiated from human pluripotent stem cells and the human dermal papilla precursor cells differentiated from human pluripotent stem cells and having hair follicle-forming ability.

The present invention also provides a use of epithelial stem cells differentiated from human pluripotent stem cells and the human dermal papilla precursor cells differentiated from human pluripotent stem cells and having hair follicle forming ability.

In one embodiment of the present invention, the dermal papilla precursor cells may be differentiated from the pluripotent stem cells for 30 days to 50 days.

In another embodiment of the present invention, the epithelial stem cells may be differentiated from the pluripotent stem cells for 15 days to 21 days.

Advantageous Effects of Invention

The inventors of the present invention developed a method of differentiating dermal papilla precursor cells having hair follicle forming ability from human pluripotent stem cells, and a medium composition of specific differentiation into dermal papilla precursor cells, and effectively induced the neogenesis of hair follicles consisting of only human cells, not conventional mouse-human hybrid hair follicles, by using human dermal papilla precursor cells obtained using the differentiation method and human epithelial stem cells. Thus, in-vitro model for differentiation into dermal papilla precursor cells according to the present invention may be used as a model for research on the development stage and differentiation process of dermal papilla cells, and human hair follicle tissue produced by the dermal papilla cell differentiation technique according to the present invention overcomes limitations of hair loss treatment, and thus is expected to be effectively used as a treatment method for patients who suffer from hair loss.

BRIEF DESCRIPTION OF DRAWINGS

FIGS. 2A to 2F illustrate the results of confirming the differentiation process and properties of dermal papilla precursor cells, wherein FIG. 2A depicts a process of differentiating dermal papilla precursor cells from human dedifferentiated pluripotent stem cells over time; FIG. 2B illustrates the results of observing the morphology of neural crest stem cells (hi-NCSCs) differentiated for 7 days, and the results showing the expression of the HNK1 and p75NTR proteins; FIG. 2C illustrates the results of observing the morphology of differentiated dermal papilla precursor cells (hi-DPPCs) and showing alkaline phosphatase (ALP) activity; FIG. 2D illustrates flow cytometry results showing the possibility of differentiating into SDC1+CD133 cells according to various factor combinations; FIG. 2E illustrates the results of performing flow cytometry on SDC1+CD133 cells after treatment with CHIR-99021 as a BIO substitute; and FIG. 2F illustrates the results showing the possibilities of various kinds of human pluripotent stem cells to differentiate into SDC1+CD133 DPPCs.

FIGS. 3A to 3C illustrate the results showing the expression patterns of various genes in a process of differentiation of dermal papilla precursor cells from human induced pluripotent stem cells, wherein FIG. 3A illustrates flow cytometry results showing changes in expression of SDC1 and CD133 in cells (iPSC, NCSC, DPPC D25, DPPC D40, and DPPC P5) of each differentiation stage during a differentiation process; FIG. 3B illustrates the results showing changes in gene expression according to stage in the cells of each differentiation stage; and FIG. 3C illustrates the results of comparing the expression levels of ALX3, CTNNB1, SOX2, LEF1, and VCAN, which are genes expressed in dermal papilla after isolating CD133+ and CD133− from dermal papilla precursor cells on day 25 of differentiation.

FIG. 4A to 4C illustrate the results of comparing the properties of human dermal papilla precursor cells (hi-DPPC) according to the present invention with those of human dermal papilla cells (hDPCs), wherein FIG. 4A illustrates the results of confirming ALP activity for the two types of cells and the expression of the αSMA, VCAN, and nestin genes through immunocytochemistry staining; FIG. 4B illustrates the results showing spontaneous sphere-forming ability; and FIG. 4C illustrates the results of comparing the expression levels of dermal papilla signature genes through transcript analysis by quantitative RT-PCR.

FIGS. 5A and 5B illustrate the results of performing patch assay using dermal papilla precursor cell spheres (hi-DPPC 3D) or dermal papilla cell spheres (hDPC 3D) in order to determine the hair follicle-forming ability of dermal papilla precursor cells according to the present invention, wherein FIG. 5A illustrates the results showing that, as a result of subcutaneous transplantation of the two types of cells along with C57BL/6 mouse-derived epidermal cells, hybrid hair follicle neogenesis was induced; and FIG. 5B illustrates the results of confirming the contribution of dermal papilla precursor cells to hair follicle neogenesis by labeling the dermal papilla precursor cells with a cell tracer (CM-DiI).

FIGS. 6A to 6D illustrates the results of confirming the gene expression profile of dermal papilla precursor cells, wherein FIGS. 6A and 6B illustrate a heatmap (FIG. 6A) and clustering results using distance matrix, obtained through RNA sequencing of neural crest stem cells (hi-NCSCs) derived from human induced pluripotent stem cells, human dermal papilla cell spheres (cDPC 3D), human dermal papilla cells (cDPC 2D), and dermal papilla precursor cell spheres (hi-DPPC 3D); FIG. 6C illustrates the results of analyzing the RNA sequencing results by a dimension reduction approach; and FIG. 6D illustrates the results of comparing the expression levels of dermal papilla signature genes and stem cell marker genes.

FIGS. 7A and 7B illustrate the results of analyzing in-vitro hair follicle neogenesis according to co-culture of human dermal papilla precursor cells and human epithelial stem cells, wherein FIG. 7A illustrates microscopic observation results showing changes in the morphology of the two types of cells due to co-culture, and FIG. 7B illustrates immunofluorescence staining results showing whether dermal marker proteins (SDC1, LEF1, SOX2, Nestin, VCAN, and WIF1) and epidermal marker proteins (CD133, BMP4, K15, K14, and WIF1) were expressed in in-vitro formed hair follicles and human fetal scalp.

FIG. 8A illustrates microscope images showing the structures of multiple root sheath and dermal papilla as a result of H&E staining of formed hair follicle tissue; FIG. 8B illustrates immunofluorescence staining results of human COX4 (hCOX4) and human mitochondria in formed hair follicles and hair follicles of fetal scalp; and FIG. 8C illustrates the results of performing immunofluorescence staining on K14, K15, K17, and K75 in formed hair follicles.

MODE OF INVENTION

Figure 1:
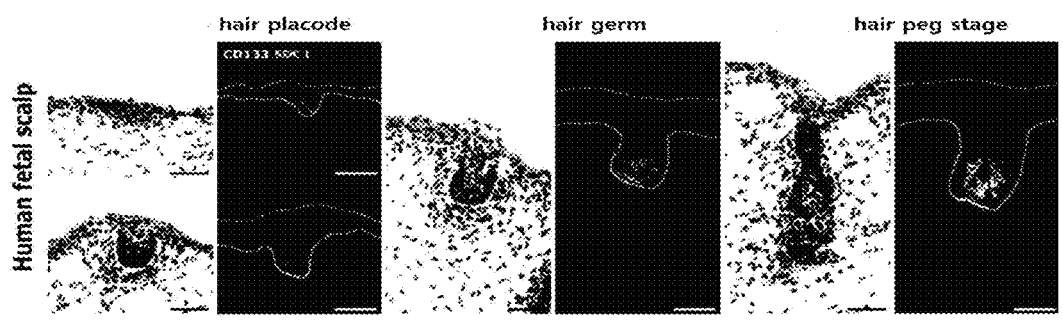
FIG. 1 illustrates the results of performing immunostaining to observe the expression of SDC1 and CD133 in hair placode, hair germ, and hair peg stage in the human fetal scalp.

The present invention relates to a medium composition for differentiation of dermal papilla precursor cells from human pluripotent stem cells, a differentiation method, and a use of dermal papilla precursor cells differentiated using the method for inducing hair follicle neogenesis.

Therefore, the present invention provides a medium composition for differentiation of dermal papilla precursor cells from human pluripotent stem cells, including Dulbecco's Modified Eagle's Medium/Nutrient Mixture F-12 (DMEM/F12) GLUTAMAX™ (L-alanyl-L-glutamine) (Reference 1) containing fibroblast growth factor-2 (FGF2), a glycogen synthase kinase-3 (GSK-3) inhibitor, and bone morphogenetic protein 4 (BMP4).

In the medium composition, the glycogen synthase kinase-3 (GSK-3) inhibitor may be one or more selected from the group consisting of 6-bromoindirubin-3'-oxime (BIO), CHIR-99021, and SB-216763, but the present invention is not limited thereto, and any glycogen synthase kinase-3 inhibitor known in the art may be used without limitation.

In medium composition, preferably, the FGF2 may be included at a concentration of 5 ng/ml to 30 ng/ml, the GSK-3 inhibitor may be included at a concentration of 0.1 μM to 10 μM, and the BMP4 may be included at a concentration of 0.5 ng/ml to 5 ng/ml. The differentiation of dermal papilla precursor cells from human pluripotent stem cells may be most effective within the above-described concentration ranges.

In the medium composition, preferably, the BIO may be included at a concentration of 0.5 μM to 5 μM, and the CHIR 99021 may be included at a concentration of 0.1 μM to 10 μM. The differentiation of dermal papilla precursor cells from human pluripotent stem cells may be most effective within the above-described concentration ranges.

In the medium composition, the human pluripotent stem cells may be human embryonic stem cells or human induced pluripotent stem cells, but the present invention is not limited thereto.

In the medium composition, preferably, human tissue may not be incorporated. The expression "human tissue is not incorporated" means that the content of human tissue incorporated into the medium composition is 5% or less, 3% or less, 1% or less, most preferably 0%, with respect to a total content of the medium composition. The 0% incorporation means that no human tissue is incorporated into the medium composition.

The present invention also provides a method of differentiating dermal papilla precursor cells from human pluripotent stem cells, including the following processes:

(a) culturing embryonic bodies of human pluripotent stem cells in a neural crest stem cell induction medium to differentiate into neural crest stem cells; and (b) culturing the differentiated neural crest stem cells in the above-described medium composition to differentiate into dermal papilla precursor cells.

Hereinafter, the medium composition and each process of the differentiation method will be described in detail.

The term "pluripotent stem cells (PSCs)" as used herein refers to stem cells having pluripotency, and PSCs may include various types of stem cells known in the art, for example, embryonic stem cells or induced pluripotent stem cells, but the present invention is not limited thereto.

The term "human pluripotent stem cells" as used herein means that the origin of pluripotent stem cells is a human, for example, tissue, blood, and the like of humans, and examples of the human pluripotent stem cells may include human embryonic stem cells, human fibroblast-derived hiPSCs (FB-derived hiPSCs), and human dermal papilla cell-derived hiPSCs (DPC-derived hiPSCs).

The term "induced pluripotent stem cells (iPSCs)" as used herein refers to cells that return to a pre-differentiated cell stage by transfecting differentiated somatic cells with cell differentiation-related genes and are induced to have pluripotency like embryonic stem cells. In 2006, Professor Shinya Yamanaka of Kyoto University produced stem cells with pluripotency like embryonic stem cells by introducing several genes into mouse skin fibroblasts, and successfully produced induced pluripotent stem cells by introducing genes into adult skin cells in 2007. The genes are SOX2, c-MYC, OCT4, and KLF4, which are also referred to as Yamanaka factors, and also in the present invention, to prepare induced pluripotent stem cells from skin fibroblasts isolated from humans, the four types of genes were introduced.

The induced pluripotent stem cells according to the present invention are produced from human skin fibroblasts, but any human adult cells capable of producing induced pluripotent stem cells are used without limitation.

The method may further include, before process (a), culturing the human pluripotent stem cells into embryonic bodies. Preferably, the present process may be performed for about 3 days to about 7 days.

The process (a) is a process of differentiating neural crest stem cells from the embryonic bodies of the human pluripotent stem cells. The neural crest stem cell induction medium may be supplemented with DMEM/F12 GLUTAMAX™ (L-alanyl-L-glutamine) (Reference 1), fibroblast growth factor-2 (FGF2), fibronectin, insulin, a $N_2$ supplement, and transferrin, but the present invention is not limited thereto.

In one embodiment of the present invention, as a result of verifying the characteristics of neural crest stem cells differentiated through process (a) and observing the morphology of the neural crest stem cells using a microscope, it was confirmed that the HNK1 and p75NTR proteins, which are neural crest markers, were expressed, demonstrating that differentiation of neural crest stem cells from the pluripotent stem cells successfully occurred.

Process (b) is a process of differentiating dermal papilla precursor cells from the neural crest stem cells differentiated in process (a). To differentiate dermal papilla precursor cells from the neural crest stem cells, the inventors of the present invention screened factors essential for differentiation into dermal papilla precursor cells in a general DMEM/F12 GLUTAMAX™ (L-alanyl-L-glutamine) (Reference 1) culture medium used in differentiation of dermal papilla-like cells from conventional neural crest stem cells, and as a result, finally demonstrated that, when FGF2, a GSK-3 inhibitor, and BMP4 were added as differentiation factors, differentiation into dermal papilla precursor cells are possible, and thus developed a medium composition for differentiation into dermal papilla precursor cells, containing the above-described factors.

Therefore, the neural crest stem cells differentiated in process (a) may be cultured in the medium for differentiation into dermal papilla precursor cells for 12 days to 40 days to differentiate into dermal papilla precursor cells.

In addition, the method may further include, after process (b), the following process:

(c) aging the differentiated dermal papilla precursor cells to obtain dermal papilla precursor cell spheres.

Process (c) is a process of proliferating the dermal papilla precursor cells differentiated in process (b) while subculturing to obtain dermal papilla precursor cell spheres.

Process (c) may be performed by culturing the differentiated dermal papilla precursor cells in a DMEM/F12 GLU-TAMAX™ (L-alanyl-L-glutamine) (Reference 1) medium supplemented with FGF2 alone.

In one embodiment of the present invention, to verify whether differentiation into dermal papilla precursor cells through the above method occurs well, microscopic observation was performed and the results showed that the morphology was changed from an astral shape to a spindle and polygonal shape similar to that of primary dermal papilla cells, and the resulting cells formed spheres and exhibited alkaline phosphatase activity.

In the differentiation method of the present invention, preferably, process (a) may be performed for 5 days to 9 days, process (b) may be performed for 11 days to 17 days, and process (c) may be performed for 7 days to 13 days, and at this time, differentiation of dermal papilla precursor cells from human pluripotent stem cells may be most effectively performed.

In the differentiation method of the present invention, preferably, the method of differentiating dermal papilla precursor cells from human pluripotent stem cells may be performed for 26 days to 50 days, more preferably 30 days to 45 days, and far more preferably about 40 days, and at this time, differentiation of dermal papilla precursor cells from human pluripotent stem cells may be most effectively performed. The starting point of the "26 days to 50 days" refers to a time point at which human pluripotent stem cells start to be applied to the differentiation method of the present invention. For example, in applying human pluripotent stem cells to the differentiation method of the present invention, when a process of forming embryonic bodies of human pluripotent stem cells is included before process (a), the process of forming embryonic bodies of human pluripotent stem cells may also be included in the period of 26 days to 50 days.

The present invention also provides human dermal papilla precursor cells differentiated from human pluripotent stem cells using the above-described differentiation method, wherein the human dermal papilla precursor cells have hair follicle-forming ability.

The dermal papilla precursor cells exhibit one or more characteristics selected from the group consisting of the following (a), (b), and (c):

(a) positive immunological characteristics for alkaline phosphatase (ALP), α-smooth muscle actin (αSMA), versican (VCAN), and nestin;

(b) structural properties of dermal papilla cells that spontaneously form spheres; and (c) genetic characteristics expressing one or more dermal papilla signature genes selected from the group consisting of ALX Homeobox 3 (ALX3), SRY-Box 2 (SOX2), Hes Related Family BHLH Transcription Factor With YRPW Motif 1 (HEY1), Bone Morphogenetic Protein 4 (BMP4), Lymphoid Enhancer Binding Factor 1 (LEF1), WNT inhibitory factor 1 (WIF1), and Versican (VCAN).

The dermal papilla precursor cells exhibit CD133(−), or exhibit CD133(−) and SDC1(+).

Figure 3A:
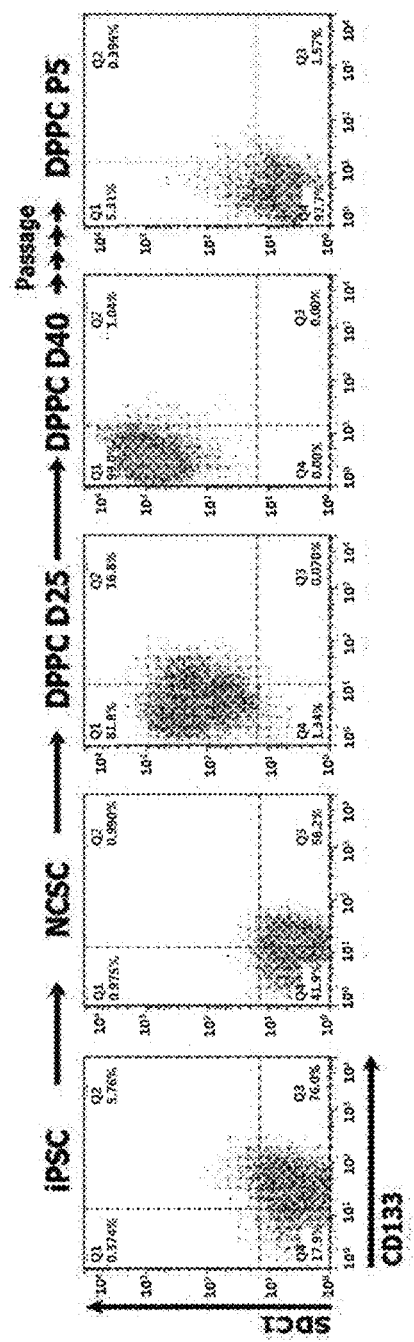
Figure 3B:
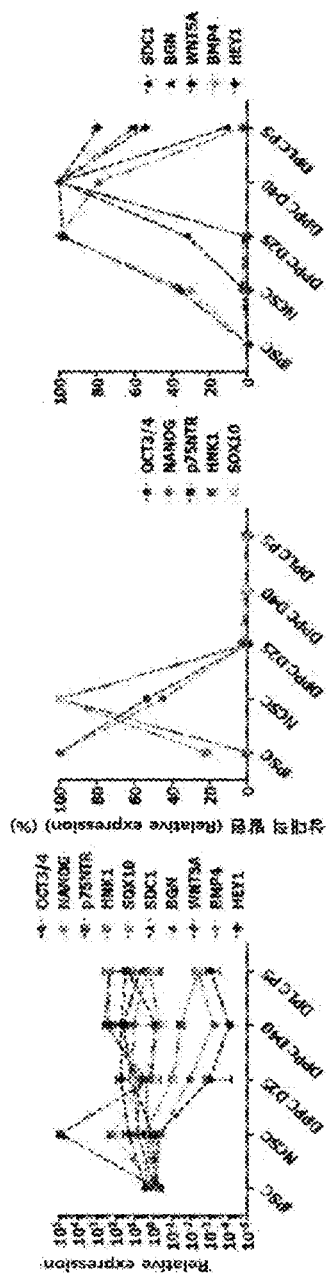
Figure 3C:
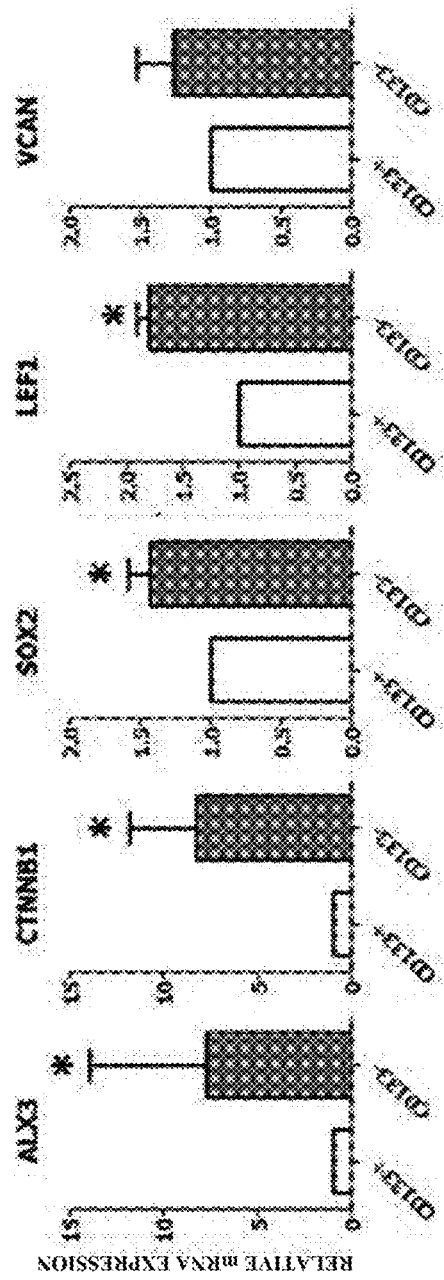

CD133 is known as a surface marker of hair-induced skin cells in mice. However, in the case of dermal papilla precursor cells according to the present invention, as illustrated in FIG. 3C, it was confirmed that the expression of genes expressed in typical dermal papilla, i.e., ALX homeobox3 (ALX3), catenin beta 1 (CTNNB1), SOX2, and lymphoid enhancer binding factor 1 (LEF1) was significantly increased in CD133-negative cells, whereas the above results were not shown in CD133-positive cells.

The present invention also provides subcultured human dermal papilla precursor cells as human dermal papilla precursor cells differentiated from human pluripotent stem cells by the differentiation method, wherein the human dermal papilla precursor cells have hair follicle-forming ability.

In one embodiment of the present invention, to verify whether the differentiated dermal papilla precursor cells have hair follicle-forming ability, the inventors of the present invention performed patch assay by subcutaneously transplanting the dermal papilla precursor cells into immunodeficient mice along with epidermal cells of C57BL/6 neonatal mice (mEPI). As a result, it was confirmed that, after 2 weeks, mouse-human hybrid hair follicle neogenesis was induced.

In another embodiment of the present invention, RNA sequencing was performed on induced neural crest stem cells, induced dermal papilla precursor cell spheres, cultured dermal papilla cell spheres, and cultured dermal papilla cells, and then gene expression profiling was analyzed. The results showed that the dermal papilla cells exhibit a gene expression pattern that was very different from that of neural crest stem cells, and highly expressed the key genes of dermal papilla cells, through which it was shown that the dermal papilla cells were similar to human dermal papilla cells and exhibited an early stage molecular signature.

Based on the above results, in another embodiment of the present invention, as a result of in-vitro co-culture of epithelial stem cells and the dermal papilla precursor cells, the formation of a spherical structure very similar to the morphology of hair follicle production and a gene expression pattern similar to human fetal scalp were observed.

In another embodiment of the present invention, chamber assay was performed using the dermal papilla precursor cells and epithelial stem cells to verify whether human hair follicle neogenesis was induced in mice. As a result, it was confirmed that, when both dermal papilla precursor cells on day 40 after differentiation started and epithelial stem cells on day 18 thereafter were transplanted into mice, the two types of cells exhibited structure and genetic characteristics similar to those of fetal hair follicles, from which it was confirmed that human hair follicle neogenesis could be induced using the dermal papilla precursor cells and epithelial stem cells, which consist of human cells alone.

Therefore, the present invention provides a composition for inducing human hair follicle neogenesis, including epithelial stem cells differentiated from human pluripotent stem cells and the human dermal papilla precursor cells as active ingredients.

The present invention also provides a method of inducing human hair follicle neogenesis by delivering, to an individual, epithelial stem cells differentiated from human pluripotent stem cells and the human dermal papilla precursor cells differentiated from human pluripotent stem cells and having hair follicle-forming ability.

The present invention also provides a method of producing human hair follicles by co-culturing human dermal papilla precursor cells differentiated from the human pluripotent stem cells and having hair follicle-forming ability and epithelial stem cells differentiated from human pluripotent stem cells. In the present invention, preferably, the co-culture may be performed in vitro.

The present invention also provides a use of a composition for human hair follicle neogenesis, the composition including, as active ingredients, epithelial stem cells differentiated from human pluripotent stem cells and the human dermal papilla precursor cells differentiated from human pluripotent stem cells and having hair follicle-forming ability.

The term "human hair follicles" as used herein means human hair follicles, but does not mean that an individual who wishes to newly form hair follicles is limited to humans, and the individual who wishes to newly form hair follicles may include various animals known in the art capable of having hair follicles, including humans. For example, the various animals known in the art capable of having hair follicles may include mammals, and the mammals may include mice and the like. According to a specific embodiment of the present invention, human hair follicle neogenesis was induced in mice.

The present invention also provides a cell therapeutic agent for treating hair loss, including epithelial stem cells differentiated from human pluripotent stem cells and the human dermal papilla precursor cells as active ingredients.

The present invention also provides a method of treating hair loss, including administering, to an individual, a cell therapeutic agent including, as active ingredients, epithelial stem cells differentiated from human pluripotent stem cells and the human dermal papilla precursor cells differentiated from human pluripotent stem cells and having hair follicle-forming ability.

The present invention also provides a use of a composition for hair loss treatment, the composition including, as active ingredients, epithelial stem cells differentiated from human pluripotent stem cells and the human dermal papilla precursor cells differentiated from human pluripotent stem cells and having hair follicle-forming ability.

The present invention also provides a method of inducing hair follicle neogenesis, including transplanting, into tissue except for humans, human epithelial stem cells and the human dermal papilla precursor cells.

The dermal papilla precursor cells may be differentiated from the human pluripotent stem cells for 30 days to 50 days, and the epithelial stem cells may be differentiated from the human pluripotent stem cells for 15 days to 21 days.

The dermal papilla precursor cells may be CD133(−), and the epithelial stem cells may be CD133(+).

Hereinafter, exemplary examples will be described to aid in understanding of the present invention. However, the following examples are provide only to facilitate the understanding of the present invention and are not intended to limit the scope of the present invention.

EXAMPLES

Example 1. Experiment Preparation and Experimental Method 1-1. Production of Induced Pluripotent Stem Cells from Human Skin Fibroblasts Human skin fibroblasts (ATCC PCS-201-012) were sub-cultured three times, and then reprogramming factors OCT4, SOX2, KLF4, and c-MYC were transduced using a retrovirus. At 24 hours after transduction, a virus-containing medium was replaced with a fresh growth medium, and two weeks after transduction, induced pluripotent stem cell (iPSC)-like colonies were observed in the transduced human skin fibroblasts. The colonies were picked up and transferred to a new STO feeder, and after 2 days of colony attachment, the culture medium was replaced with a fresh embryonic stem cell culture medium supplemented with 10 ng/ml of bFGF.

Subsequently, the embryonic stem cell culture medium was replaced daily, the colonies were incubated under 5% $O_2$ conditions on a mitomycin C-inactivated mouse STO feeder in a human embryonic stem cell medium containing DMEM/F12 GLUTAMAX™ (L-alanyl-L-glutamine) (Reference 1) (Thermo Fisher, catalog no. 10565042), 20% knockout serum replacement (Thermo Fisher), 1% non-essential amino acids (Invitrogen), 2 mM glutamine (Thermo Fisher), 0.1 mM (3-mercaptoethanol (Thermo Fisher), and 10 ng/ml of bFGF (Thermo Fisher). The subculture was performed using a general method or 1 mg/ml of collagenase-type IV (Thermo Fisher) at intervals of 5 days to 7 days. All parental lineages were maintained for 50 passages or more, and it was confirmed that OCT3/4, NANOG, and SSEA4 were stably expressed.

1-2. Differentiation of Neural Crest Stem Cells from Human Induced Pluripotent Stem Cells First, to form embryonic bodies (EBs), when the colonies of induced pluripotent stem cells reached 80% to 90% of the area of a culture dish, the colonies were treated with 2 mg/ml of collagenase IV at 37° C. for 1 hour, the differentiated colonies were separated with a pipette tip, and then the separated colonies were gently collected. Subsequently, the supernatant was discarded, the resulting colonies were resuspended in a culture medium of the induced pluripotent stem cells, which was free of bFGF, and then embryonic bodies were transferred to 10 cm culture dishes and cultured in 8 ml of the medium per culture dish. The next day, the medium was replaced, an aggregate was further cultured for 5 days, and the induced pluripotent stem cell culture medium was supplemented every other day.

After culture, the embryonic bodies were dispensed onto cell culture dishes coated with 15 µg/ml of poly-L-ornithine (Sigma-Aldrich) and 10 µg/ml of fibronectin (BD), and cultured overnight in an $N_2$ medium of the following composition. DMEM/F12 GLUTAMAX™ (L-alanyl-L-glutamine) (Reference 1) (Thermo Fisher, catalog no. 10565042), 1% $N_2$ supplement (Thermo Fisher), 20 µg/ml of insulin (Sigma-Aldrich), 0.1 mg/ml of transferrin (Sigma-Aldrich), 20 ng/ml of bFGF (Thermo Fisher), 2.5 µg/ml of fibronectin (Sigma-Aldrich), 1× penicillin/streptomycin. The medium was replaced daily.

1-3. Differentiation of Dermal Papilla Precursor Cells from Neural Crest Stem Cells (1) Development of Medium Composition To develop a dermal papilla precursor cell medium composition for inducing differentiation of dermal papilla precursor cells from neural crest stem cells, the possibility of differentiation into dermal papilla precursor cells was examined by treatment with several factors alone known as vital materials for dermal papilla cell differentiation or a combination thereof. To confirm differentiation into dermal papilla precursor cells, mouse anti-human SDC1 and CD133/2 antibodies were stained using PBS supplemented with 2% FBS, and then the stained cells were analyzed using a flow cytometer (BD Biosciences).

A DMEM/F12 GLUTAMAX™ (L-alanyl-L-glutamine) (Reference 1) (Thermo Fisher, catalog no. 10565042), 10% FBS basal medium was treated with one of a GSK-3 inhibitor (6-Bromoindirubin-3'-oxime (BIO)), bFGF, BMP4, purmophamine, and EGF, treated with a combination of two of a GSK-3 inhibitor (6-Bromoindirubin-3'-oxime (BIO)), bFGF, and BMP4, or treated with all of a GSK-3 inhibitor (6-Bromoindirubin-3'-oxime (BIO)), bFGF, and BMP4, and after about 2 weeks, dermal papilla precursor cells, differentiation of which was induced from neural crest stem cell, were analyzed using SDC1 and CD133, and the analysis results showed that the differentiated cells were significantly increased only in a group treated with all of a GSK-3 inhibitor (6-Bromoindirubin-3'-oxime (BIO)), bFGF, and BMP4.

(2) Differentiation of Dermal Papilla Precursor Cells from Neural Crest Stem Cells To induce differentiation of dermal papilla precursor cells from neural crest stem cells, neural crest stem cells were induced from embryonic bodies at 50% to 60% of the culture area for 5 days. The differentiation-induced neural crest stem cells were cultured in a dermal papilla precursor cell differentiation medium containing DMEM/F12 GLUTAMAX™ (L-alanyl-L-glutamine) (Reference 1) (Thermo Fisher, catalog no. 10565042), 10% FBS, a GSK-3 inhibitor (1 µM 6-bromoindirubin-3'-oxime (BIO)) (Sigma-Aldrich)), 20 ng/ml of bFGF, 1× penicillin/streptomycin without subculture, and the medium was replaced every other days.

Spindle-shaped neural crest stem cells changed when 1 ng/ml of human recombinant bone morphogenetic protein 4 (BMP4) (R&D Systems) was added to the dermal papilla precursor cell differentiation medium at time at which the cell shape was changed to a shape similar to that of fibroblasts for 2 days.

After about 2 weeks, the isolated dermal papilla precursor cells were washed with PBS, 1 ml of Tryple express (Life technologies) was added thereto, followed by incubation at 37° C. for 5 minutes, and the dermal papilla precursor cells were recovered with PBS and centrifuged at 1,200 rpm and room temperature for 5 minutes. For initial passages, 1:2 or 1:3 culture was performed in uncoated culture dishes using a dermal papilla precursor cell differentiation medium free of BIO (Sigma-Aldrich) and human recombinant BMP4 (R&D Systems). After the passages, it was confirmed that most undifferentiated cells were not attached and only the differentiated dermal papilla precursor cells survived.

(3) Use of CHIR-99021 as GSK-3 Inhibitor

To determine the role of a GSK-3 inhibitor as a WNT signal activator in the dermal papilla precursor cell medium composition for inducing differentiation of dermal papilla precursor cells from neural crest stem cells, the possibility of differentiation into dermal papilla precursor cells was examined by treatment with not only 6-bromoindirubin-3'-oxime (BIO) but also CHIR-99021 at 0.1 µM, 1 µM, and 10 µM. To confirm the possibility of differentiation into dermal papilla precursor cells, mouse anti-human SDC1 and CD133/2 antibodies were stained using PBS supplemented with 2% FBS, and then the stained cells were analyzed using a flow cytometer (BD Biosciences).

A DMEM/F12 GLUTAMAX™ (L-alanyl-L-glutamine) (Reference 1) (Thermo Fisher, catalog no. 10565042), 10% FBS basal medium was treated with all of a GSK-3 inhibitor (CHIR-99021), bFGF, and BMP4, and after about 2 weeks, neural crest stem cells, differentiation of which was induced from human pluripotent stem cells, were subjected to flow cytometry using dermal papilla precursor cell markers SDC1 and CD133, and from the results, it was confirmed that differentiation efficiency increased according to the concentration of GSK-3 inhibitor (CHIR-99021), through which concentration-dependent differentiation induction patterns as well as the importance of WNT signal activation were confirmed in differentiation into dermal papilla precursor cells.

1-4. Differentiation of Epithelial Stem Cells from Human Induced Pluripotent Stem Cells Differentiation of epithelial stem cells (EpSCs) from induced pluripotent stem cells obtained by dedifferentiation from human skin fibroblasts in Example 1-1 was carried out according to a conventionally known differentiation protocol. Briefly, before differentiation, induced pluripotent stem cells were isolated by treatment with 2 mg/ml of collagenase IV (Thermo Fisher) at 37° C. for 1 hour, and cell aggregates were grown for 24 hours in an embryonic stem cell medium containing 1 ng/ml of human recombinant BMP4. On day 2, embryonic bodies were collected and the supernatant was discarded, and then the cultures were dispensed into STO cells treated with mitomycin-C. The dispensed cells were grown in a differentiation medium containing 1 µM all-trans RA (Sigma-Aldrich), and after 2 days, the cells of the ectoderm lineage migrated from the embryonic bodies, the medium was replaced with a differentiation medium containing 25 ng/ml of human recombinant BMP4, 20 ng/ml of human EGF (Sigma-Aldrich), and 1 µM all-trans RA, and then the cells were cultured in the differentiation medium until clones of the epithelial stem cells were observed, and isolated on about day 11. In the differentiated epithelial stem cells, the amount of CD200+/ITGA6+ cells reached the maximum level on about day 18 after culture, and the CD200+/ITGA6+ cells were isolated through MACS analysis, and then used in hair follicle neogenesis experiments.

1-5. Isolation and Culture of Human Dermal Papilla Cells

To obtain human dermal papilla cells (hDPCs), skin biopsy samples (1.5 cm×1.0 cm scalp tissue samples at the occiput) were taken from healthy male volunteers (mean age: 36.6±9.4 years old). Human dermal papilla cells were isolated from each hair follicle which is considered to be morphologically growing, and the isolated dermal papilla cells were incubated in Dulbecco's Modified Eagle's Medium (DMEM)(Welgene) supplemented with 10% FBS (Thermo Fisher) and 1× penicillin/streptomycin (Thermo Fisher) at 37° C. under 5% $CO_2$.

1-6. Histology and Immunofluorescence Staining

Scalp tissue from human fetuses was mounted on Tissue-Tek cryo-OCT (Fisher Scientific) and frozen using methyl butane/dry ice. Tissue blocks were cut to a thickness of 10 Vim at 25° C. and stored at 80° C. until immunofluorescence staining was performed.

1-7. Staining of Antibody Against Cell Membrane Proteins

Tissue embedded in paraffin was cut to a thickness of 4 µm, and the obtained sections were stained with hematoxylin & eosin. In other cases, for antigen searching, sections of 4 µm-thick microcut tissue were treated with citrate buffer (DAKO) at 120° C. for 15 minutes.

Meanwhile, the frozen tissues cleaved for antibody staining were fixed with 4% paraformaldehyde for 20 minutes, and then the fixed tissues were incubated with an Ultravision protein blocking solution (Thermo Fisher) for 30 minutes. Next, the cells were treated with primary antibodies and cultured, and then treated with a solution obtained by diluting secondary antibodies and an antibody dilution solution (Life Technologies) at a ratio of 1:200, followed by culture for 1 hour and washing. Thereafter, the cells were counterstained with 4',6-diamidino-2-phenylindole (DAPI) (Thermo Fisher), and then mounted on immuno-mount (Thermo Fisher).

1-8. Staining of Antibody Against Transcription Factors

The frozen tissue sections fixed with 4% paraformaldehyde or formed human hair follicles were treated with a blocking solution containing 0.01% saponin (Sigma-Aldrich) and 0.25% fish gelatin (Sigma-Aldrich) to increase cell membrane permeability. Thereafter, primary and secondary antibody staining was performed using a blocking solution, and the cells were treated with isotype control to confirm background staining in each experiment.

1-9. Flow Cytometry and Cell Sorting

Induced pluripotent stem cells (iPSCs), neural crest stem cells (NCSCs), and dermal papilla precursor cells (DPPCs) (Day 25, 40, Passage 5) were incubated with mouse anti-human SDC1, CD133/2, and SSEA3, and staining was performed using PBS supplemented with 2% FBS. Subsequently, the stained cells were analyzed using an LSR™ II flow cytometer (BD® LSRII Flow Cytometer).

For cell sorting, cells were isolated in PBS at a concentration of $10^6$ cells/ml using an ARIA™ II cell separator (BD FACS ARIA™ II). A Miltenyi MACS bead separation system was used for magnetic bead separation according to the manufacturer's instructions and separation conditions. The results were analyzed using FLOWJO™ software (FlowJo, LLC).

1-10. Hair Follicle Neogenesis Analysis Through Patch Assay

Before performing hair follicle neogenesis analysis, SSEA3- cells were isolated from human induced pluripotent stem cell-derived dermal papilla precursor cells (hiPSC-derived DPPCs) through MACS analysis and undifferentiated cells were removed. 20 μl of 10% DMEM containing $1 \times 10^4$ of the sorted dermal papilla precursor cells or the cultured human dermal papilla cells was added dropwise onto the lid of each petri-dish. Dermal papilla cell spheres or human induced pluripotent stem cell-derived dermal papilla precursor cell spheres were dispensed and obtained after 48 hours. Cultured human dermal papilla cells or human induced pluripotent stem cell-derived dermal papilla precursor cells were incubated with epithelial cells of C57BL/6 neonatal mice or human induced pluripotent stem cell-derived CD200+/ITGA6+/SSEA3 cells. In all experiments, cultured human dermal papilla cells (a total of $1 \times 10^6$, 100 spheres) or human induced pluripotent stem cell-derived dermal papilla precursor cells (a total of $1 \times 10^6$, 100 spheres) and epithelial cells ($5 \times 10^5$ cells) were mixed in DMEM/F12 GLUTAMAX™ (L-alanyl-L-glutamine) (Reference 1) and the resulting mixture was subcutaneously injected into severe combined immunodeficient hairless outbred (SHO) female mice aged 7 weeks (18 g-20 g; Jackson Laboratory). To confirm the origin of human dermal papilla precursor cells in the formed hair follicles, the dermal papilla precursor cells were labeled with a fluorescent dye reagent, CM-DiI (Invitrogen). Host mice were sacrificed at week 5 to week 6 after transplantation to obtain a regenerated hair follicle structure. The present experiment was approved by Seoul National University Hospital Institutional Review Board (Approval No. 15-0178-C1A0).

1-11. Hair Follicle Neogenesis Analysis Through Chamber Assay

Cells were prepared in the same manner as described in the patch assay above. Briefly, human induced pluripotent stem cell-derived dermal papilla precursor cells (hiPSC-DPPC) (a total of $5 \times 10^6$, 500 spheres) and human induced pluripotent stem cell-derived epithelial stem cells ($5 \times 10^6$ cells), which were co-cultured in DMEM/F12 GLUTAMAX™ (L-alanyl-L-glutamine) (Reference 1), were transferred to a silicone chamber implanted in the back epidermis of each SHO mouse. After 2 weeks, the chamber was removed and the implanted site was subjected to dressing, and then 5 weeks later, the implanted site was obtained for histological analysis.

1-12. Quantitative Reverse Transcription Polymerase Chain Reaction

Total RNA was isolated from induced pluripotent stem cells, neuronal stem cells, dermal papilla precursor cells, 2D cultured dermal papilla cells, and 3D cultured dermal papilla cells using RNAiso Plus (Takara Bio). cDNA was synthesized using the isolated RNA as a template using a REVERT AID™ First strand cDNA synthesis kit (Thermo Fisher). Thereafter, quantitative reverse transcription polymerase chain reaction analysis was performed using SYBR premix Ex Taq II (Takara Bio), and the used primer sequences are shown in Table 1 below.

TABLE 1

| GENE | DIRECTION | SEQUENCE (5'-3') | SEQ ID NO |
|---|---|---|---|
| SDC1 | Forward | CTCTGTGCCTTCGTCTTTCC | 1 |
|  | Reverse | CCACCTTCCTTTGCCATTTA | 2 |
| BGN | Forward | GTCTATCTGCACTCCAACAA | 3 |
|  | Reverse | TGGATGGCCAGGCGGTCAGT | 4 |
| BMP4 | Forward | GCCCGCAGCCTAGCAA | 5 |
|  | Reverse | CGGTAAAGATCCCGCATGTAG | 6 |
| HEY1 | Forward | GCGCACGCCCTTGCT | 7 |
|  | Reverse | GCCAGGCATTCCCGAAA | 8 |
| WIF1 | Forward | TGGCATGGAAGACACTGCAA | 9 |
|  | Reverse | GGCCTCAGGGCATGTATGA | 10 |
| WNT5A | Forward | AGGGCTCCTACGAGAGTGCT | 11 |
|  | Reverse | GACACCCCATGGCACTTG | 12 |
| OCT3/4 | Forward | GACAGGGGGAGGGGAGGAGCTAGG | 13 |
|  | Reverse | CTTCCCTCCAACCAGTTGCCCCAAAC | 14 |
| NANOG | Forward | CCTGTGATTTGTGGGCCTG | 15 |
|  | Reverse | GACAGTCTCCGTGTGAGGCAT | 16 |
| p75NTR | Forward | CCCCCTTCTCCCACACTGCTA | 17 |
|  | Reverse | AACCCCAAACCTGACTCCAT | 18 |
| HNK1 | Forward | GCAAGAAGGGCTTCACTGAC | 19 |
|  | Reverse | GCCCCCAGAATAGAAAGGAG | 20 |
| SOX10 | Forward | AGCCCAGGTGAAGACAGAGA | 21 |
|  | Reverse | AGGAGAAGGCCGAGTAGAGG | 22 |
| ALX3 | Forward | GAATGAGCTGCCCACCTCTT | 23 |
|  | Reverse | CCTGTAACGTGTTCCCTGCT | 24 |
| CTNNB1 | Forward | CTGCCATCTGTGCTCTTCGT | 25 |
|  | Reverse | CAGTGGGATGGTGGGTGTAA | 26 |
| SOX2 | Forward | TGCGAGCGCTGCACAT | 27 |
|  | Reverse | TTCTTCATGAGCGTCTTGGTTTT | 28 |
| LEF1 | Forward | ATTCCGGGTACATAATGATGCC | 29 |
|  | Reverse | GAGAAAAGTGCTCGTCACTGT | 30 |
| VCAN | Forward | TGTTCCTCCCACTACCCTTG | 31 |
|  | Reverse | CTTCCACAGTGGGTGGTCTT | 32 |
| NOG | Forward | CCTCATCGAACACCCAGAC | 33 |
|  | Reverse | CATGAAGCCTGGGTCGTAGT | 34 |

TABLE 1-continued

| GENE | DIRECTION | SEQUENCE (5'-3') | SEQ ID NO |
|---|---|---|---|
| GAPDH | Forward | ATTGTTGCCATCAATGACCC | 35 |
|  | Reverse | AGTAGAGGCAGGGATGATGT | 36 |
| OCT4 (endo) | Forward | CCTCACTTCACTGCACTGTA | 37 |
|  | Reverse | CAGGTTTTCTTTCCCTAGCT | 38 |
| SOX2 (endo) | Forward | CCCAGCAGACTTCACATGT | 39 |
|  | Reverse | CCTCCCATTTCCCTGTTTT | 40 |
| NANOG (endo) | Forward | TGAACCTCAGCTACAAACAG | 41 |
|  | Reverse | TGGTGGTAGGAAGAGTAAAG | 42 |
| REX1 | Forward | TCGCTGAGCTGAAACAAATG | 43 |
|  | Reverse | CCCTTCTTGAAGGTTTACAC | 44 |
| TERT | Forward | TGTGCACCAACATCTACAAG | 45 |
|  | Reverse | GCGTTCTTGGCTTTCAGGAT | 46 |

1-13. Alkaline Phosphatase Activity

Alkaline phosphatase activity for cells dispensed onto a plate was analyzed. More specifically, the cells were fixed with 4% paraformaldehyde for 20 minutes, and then treated with a solution obtained by diluting NBT/BCIP (Roche) in NTMT buffer for 20 minutes.

1-14. RNA Sequencing

Total RNA was isolated from human neural crest stem cells, human dermal papilla precursor cells, cultured dermal papilla cells, and cultured dermal papilla cell spheres using RNAiso Plus (Takara Bio). Next, a transcript library for 1 μg of the isolated RNA was prepared using an Illumina's TRUSEQ® Stranded mRNA kit. Poly(A)+ RNA was isolated using AMPure XP beads (Beckman Coulter) and fragmented using an Ambion Fragmentation Reagents kit (Ambion, Austin, Tex., USA). cDNA synthesis, terminal repair, base addition, and conjugation of Illumina indexed adapters were all performed according to the Illumina's protocol. The library was selected to a size of 250300 bp using BluePipin (Sage Science, MA, USA) and amplified by 14 cycles of PCR using Phusion DNA polymerase (New England Biolabs), and the amplified library was purified with AMPure XP beads. The quality of the library was evaluated by measuring the size and concentration thereof using an Agilent 2100 Bioanalyzer.

A bilateral terminal library was then sequenced using ILLUMINA® HISEQ® 2000 (2×100 nucleotide read length), and reads having passed through a purity filter of Illumina BaseCall software were used for subsequent analysis. R package "Cuffdiff" was used for differentially expressed gene analysis, and for the production of a heatmap of a total of 3,065 genes, hierarchical clustering analysis was performed on genes with a q value of less than 0.05. In addition, distance matrix analysis, multidimensional scaling plots, and gene cluster analysis were performed using R package "CummeRbund". To generate 50 clusters out of a total of 3,471 genes, gene cluster analysis was performed on important genes with an alpha value of less than 0.01.

1-15. Accession Codes

The raw data of RNA sequencing received accession number GSE100793 and was deposited in NCBI Gene Expression Omnibus.

1-16. Statistical Analysis

Gene expression and flow cytometry results were analyzed using a Student's t test or ANOVA, and qPCR results were analyzed after correction with β-actin. $p<0.05$ was considered to be statistically significant.

Example 2. Expression Analysis of SDC1 and CD133 in Human Hair Follicle Placode Stage In Vivo To induce human hair follicle neogenesis, the inventors of the present invention established a simple strategy to mimic the biological state of the hair placode stage based on the morphogenesis of hair follicles occurring in human embryos. More specifically, it was focused to obtain dermal papilla precursor cells in the dermis and skin fibroblasts at a hair follicle placode stage.

To monitor the differentiation process, specific surface markers for human dermal papilla precursor cells were needed. Syndecan-1 (SDC1) is a well-known surface marker that is strongly expressed in the scalp of human fetuses not only in mouse skin but also in the hair follicle placode stage, and is also known as a human dermal papilla signature gene. Meanwhile, CD133 was originally known as a surface marker of hair-derived dermal papilla cells in mice, but human dermal papilla cells have been reported to have no expression pattern similar to that in mice. Therefore, the inventors of the present invention first verified the expression of SDC1 and CD133 in the scalp skin of human embryos aged 16 weeks.

As a result, as shown in FIG. 1, it was confirmed that SDC1 was predominantly expressed in the dermis when the epidermal placode and the dermis were formed. In addition, although CD133 expression was not observed in the dermis at a very early stage, these results are similar to those observed in morphogenesis of hair follicles in mouse embryos. CD133 was expressed in epidermal placode cells along cells and peaks and flanks thereof, consistent with reports on the scalp of human fetuses.

Example 3. Preparation of Differentiation Medium of Human Dermal Papilla Precursor Cells (1) Production of Human Induced Pluripotent Stem Cells (hiPSC)

In accordance with known methods (Cell 131, 861-872), the inventors of the present invention produced induced pluripotent stem cells (hiPSCs) from isolated adult dermal fibroblasts using four genes called Yamanaka factors, i.e., octamer-binding transcription factor 4 (OCT4), sex determining region Y-box 2 (SOX2), Kruppel-like factor 4 (KLF4), and c-MYC. Induced pluripotent stem cell clones dedifferentiated using the method exhibited human embryonic stem cell (hESC) morphology and a high level of alkaline phosphatase (ALP) activity, and were confirmed to express various pluripotent markers including surface antigen stage-specific embryonic antigen 4 (SSEA4) as well as OCT3/4 and NANOG. It was also confirmed through quantitative real-time polymerase chain reaction (qPCR) that the expression of endogenous stemness genes including OCT3/4, SOX2, NANOG, REX1, and telomerase reverse transcriptase (TERT) was increased. In addition, teratoma formation analysis was performed to confirm the pluripotency of the induced pluripotent stem cell clones, and the clones were used as pluripotent stem cells after 100 or more consecutive passages.

(1) Differentiation of Dermal Papilla Precursor Cells from Human Pluripotent Stem Cells Next, based on the study results showing that dermal papilla precursor cells originate from neural crest stem cells in the embryonic development stage, the inventors of the present invention attempted to differentiate dermal papilla precursor cells from the induced pluripotent stem cells using neural crest stem cells as an intermediate. To this end, to produce neural crest stem cells from the human induced pluripotent stem cells, first, embryonic bodies of the induced pluripotent stem cells were cultured in a $N_2$ differentiation medium supplemented with fibroblast growth factor-2 (FGF2), fibronectin, and the like. After culture for 1 week, it was verified through immunocytochemical staining whether the HNK11 and p75NTR proteins, which are neural crest markers, were expressed on the cultured cells. As a result, it was confirmed as illustrated in FIG. 2B that the HNK1 and p75NTR proteins were expressed.

(2-1) Development of Specific Differentiation Medium Composition for Dermal Papilla Precursor Cells Next, to develop a specific differentiation medium composition for dermal papilla precursor cells, the inventors of the present invention screened essential factors for differentiation of dermal papilla precursor cells other than Dulbecco's Modified Eagle's Medium (DMEM)/F12 GLUTAMAX™ (L-alanyl-L-glutamine) (Reference 1) supplemented with 10% fetal bovine serum (FBS). In particular, it was focused to discover essential factors capable of maintaining intrinsic characteristics and endogenous molecular signatures of human dermal papilla cells or restoring the intrinsic dermal papilla characteristics during in vitro culture. As a result of conducting experiments, initial candidates containing signaling molecules such as WNT, fibroblast growth factor (FGF), bone morphogenetic protein 4 (BMP4), platelet-derived growth factor (PDGF), Sonic hedgehog (SHH), endothelin 3 (EDN3), and the like were obtained, and it was finally confirmed that, when three essential factors FGF2, 6-bromoindirubin-3'-oxime (BIO), and BMP4 were used, the differentiation of dermal papilla precursor cells could be induced.

More specifically, a DMEM/F12 GLUTAMAX™ (L-alanyl-L-glutamine) (Reference 1) (Thermo Fisher, catalog no. 10565042), 10% FBS basal medium was treated with one of a GSK-3 inhibitor (6-bromoindirubin-3'-oxime (BIO)), bFGF, BMP4, purmophamine, and EGF, treated with a combination of two of a GSK-3 inhibitor (6-bromoindirubin-3'-oxime (BIO)), bFGF, and BMP4, or treated with all of a GSK-3 inhibitor (6-bromoindirubin-3'-oxime (BIO)), bFGF, and BMP4, and after about 2 weeks, dermal papilla precursor cells, differentiation of which was induced from neural crest stem cells, were analyzed using SDC1 and CD133. As a result, it was confirmed that the cell fraction of SDC1+/CD133−, which is a marker of dermal papilla precursor cells, was significantly increased only in the group treated with all of a GSK-3 inhibitor (6-bromoindirubin-3'-oxime (BIO), bFGF, and BMP4 (see FIG. 2D).

Figure 2A:
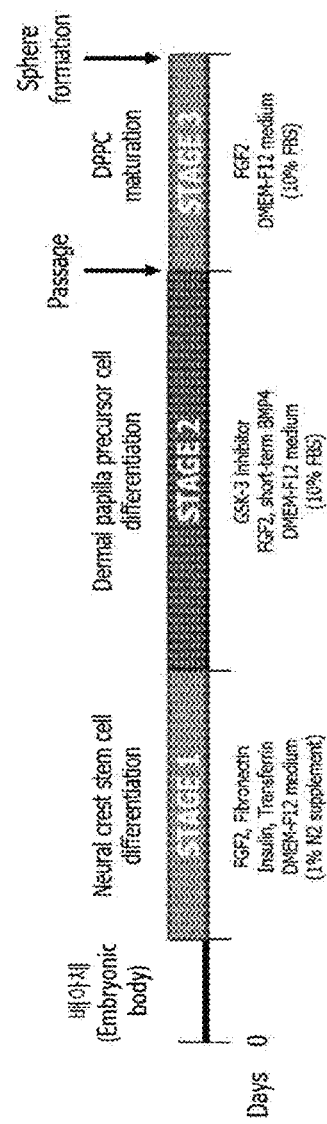
Figure 2B:
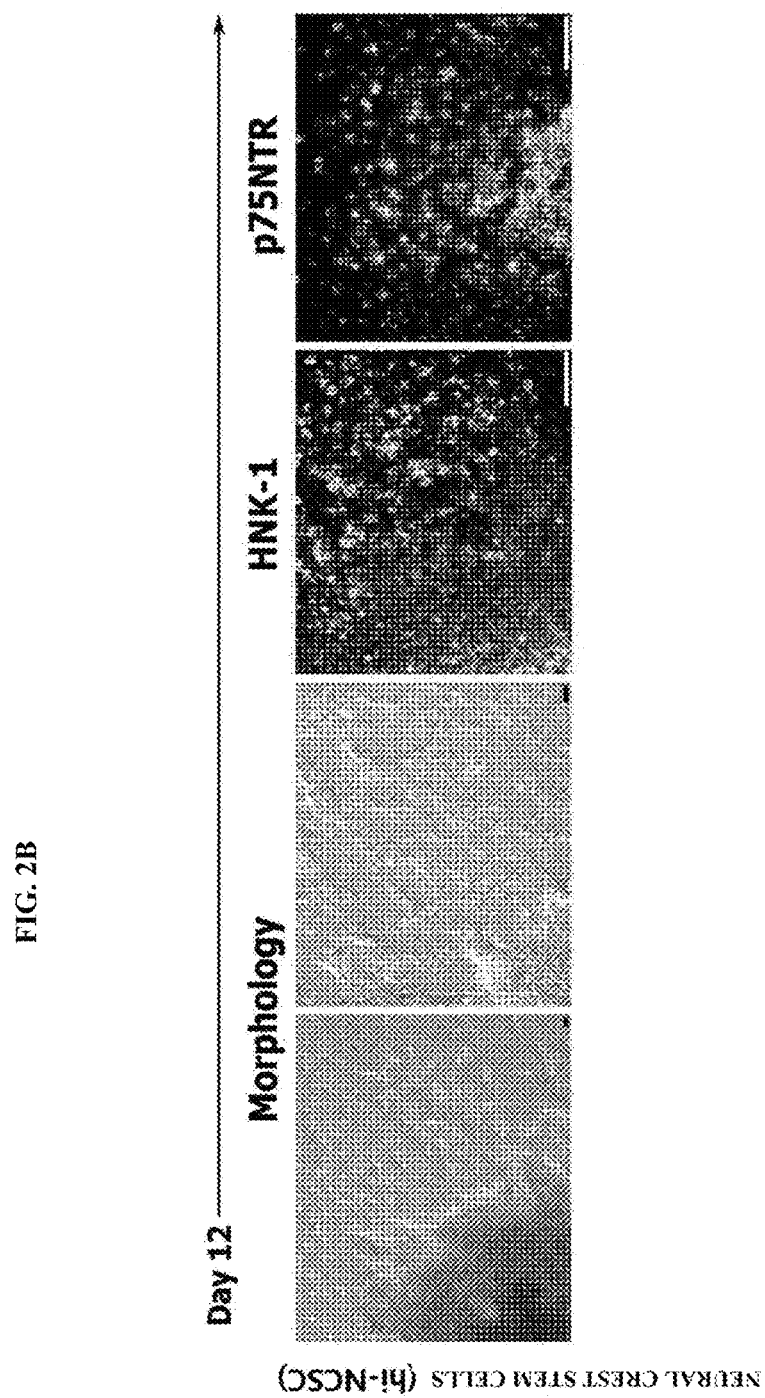
Figure 2C:
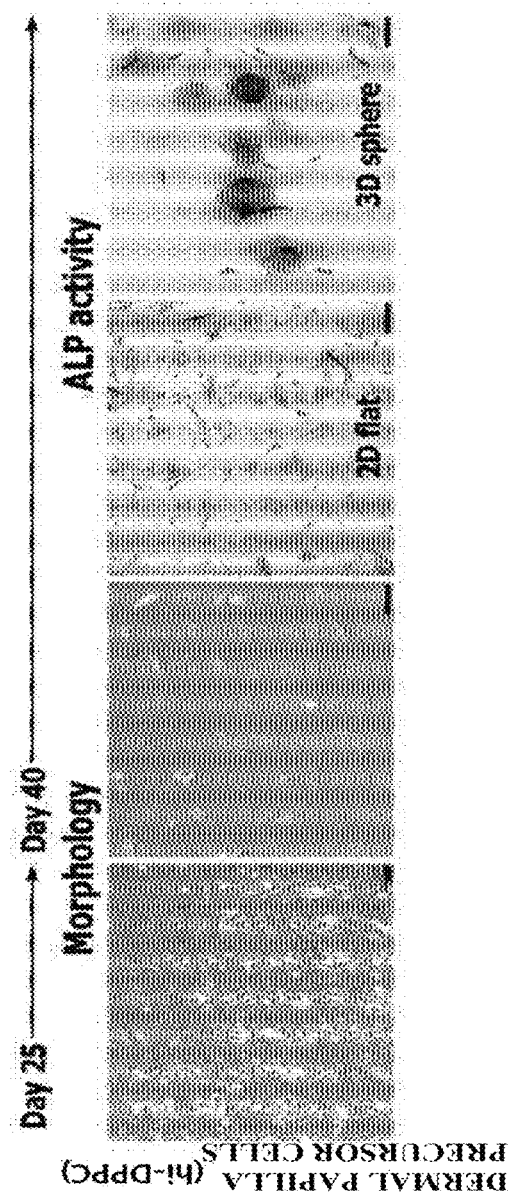
Figure 2D:
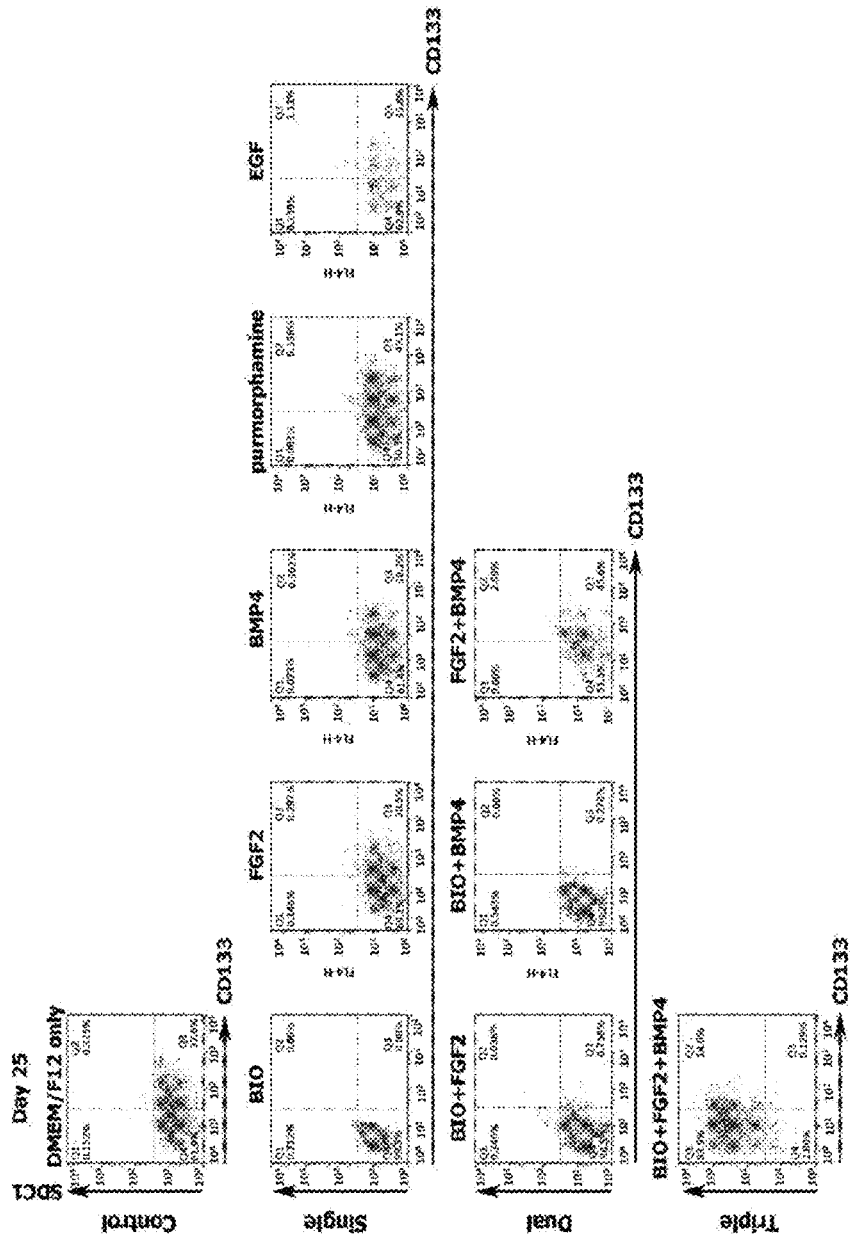
Figure 2E:
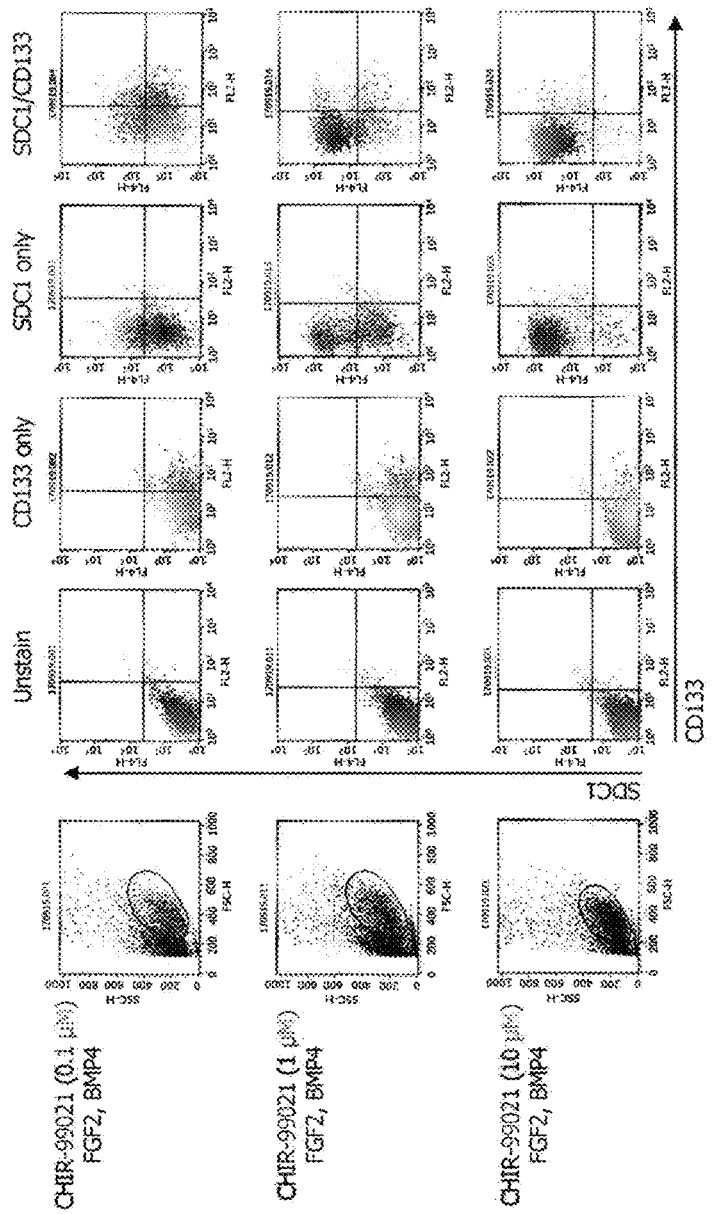

(2-2) Use of CHIR-99021 as GSK-3 Inhibitor (see FIG. 2E)

To confirm the role of a GSK-3 inhibitor as a WNT signaling activator in a dermal papilla precursor cell differentiation medium composition, the possibility of differentiation into dermal papilla precursor cells was examined by treatment with not only 6-bromoindirubin-3'-oxime (BIO) but also CHIR-99021 at 0.1 µM, 1 µM, and 10 µM. A DMEM/F12 GLUTAMAX™ (L-alanyl-L-glutamine) (Reference 1) (Thermo Fisher, catalog no. 10565042), 10% FBS basal medium was treated with all of a GSK-3 inhibitor (CHIR-99021), bFGF, and BMP4, and after about 2 weeks, dermal papilla precursor cells, differentiation of which was induced from neural crest stem cells, were subjected to flow cytometry using dermal papilla precursor cell markers SDC1 and CD133, and from the results, it was confirmed that differentiation efficiency increased according to the concentration of GSK-3 inhibitor (CHIR-99021), through which concentration-dependent differentiation induction patterns as well as the importance of WNT signal activation were confirmed in differentiation into dermal papilla precursor cells (see FIG. 2E).

Figure 2F:
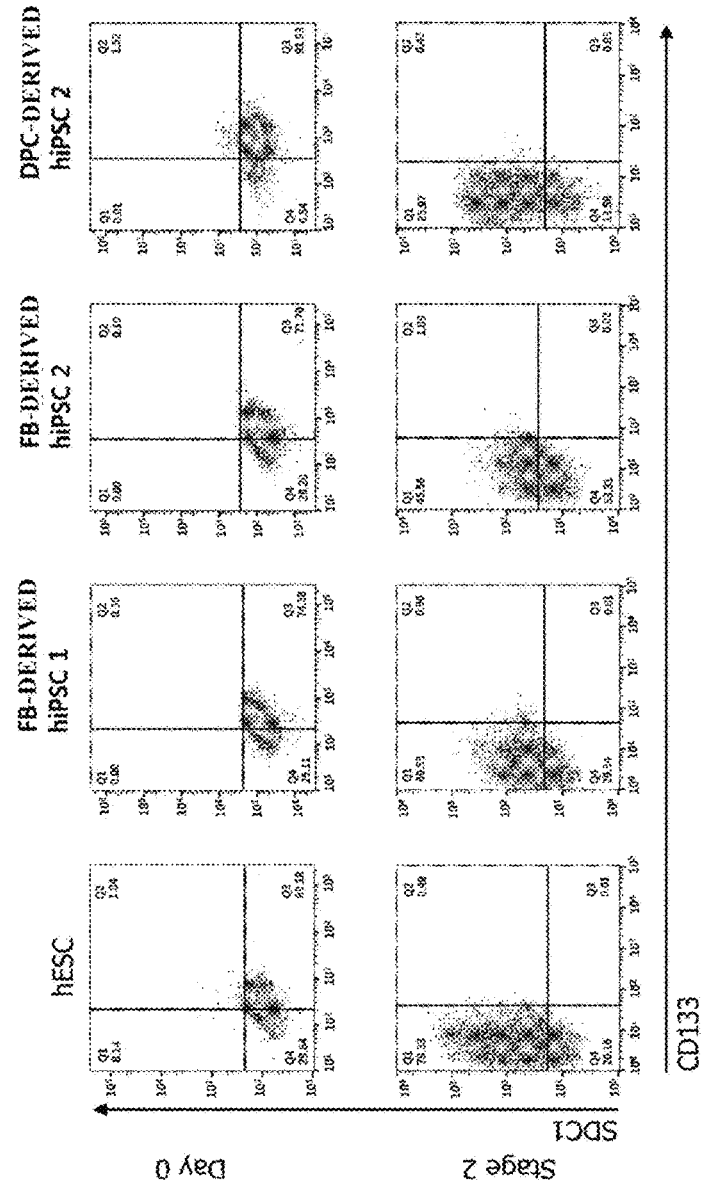

(2-3) Differentiation of Dermal Papilla Precursor Cells from Various Types of Pluripotent Stem Cells Including Induced Pluripotent Stem Cells See FIG. 2F)

To confirm whether the dermal papilla precursor cell differentiation medium composition is commonly applicable to various human cell-derived induced pluripotent stem cells including human embryonic stem cells, the possibility of differentiation into dermal papilla precursor cells was examined using, as the origins of human pluripotent stem cells, one-week-old human embryonic stem cells, two-week-old human fibroblast-derived induced pluripotent stem cells, and one-week-old human dermal papilla cell-derived induced pluripotent stem cells. A DMEM/F12 GLUTAMAX™ (L-alanyl-L-glutamine) (Reference 1) (Thermo Fisher, catalog no. 10565042), 10% FBS basal medium was treated with all of a GSK-3 inhibitor (CHIR-99021), bFGF, and BMP4, and after about 2 weeks, neural crest stem cells, differentiation of which was induced from human pluripotent stem cells, were subjected to flow cytometry using dermal papilla precursor cell markers SDC1 and CD133, and it was confirmed from the results that, although there was a difference in differentiation efficiency according to the origin of pluripotent stem cells, the cell fraction of SDC1+/CD133−, which is a dermal papilla precursor cell marker, was significantly increased in all pluripotent stem cell lines (see FIG. 2F).

(2-4) Induction of Differentiation of Dermal Papilla Precursor Cells

To induce differentiation of dermal papilla precursor cells using the essential factors selected as above, as illustrated in FIG. 2A, human induced pluripotent stem cells were differentiated into neural crest stem cells using the above-described method (STAGE 1), and then the differentiated cells were cultured in DMEM/F12 GLUTAMAX™ (L-alanyl-L-glutamine) (Reference 1) medium supplemented with FGF2 (10 ng/mL), a GSK-g inhibitor, and BMP4 (1 ng/mL) for a short time to differentiate into dermal papilla precursor cells (STAGE 2), and subsequently, surrounding dermal papilla cell-like cells were proliferated by subculture in DMEM/F12 GLUTAMAX™ (L-alanyl-L-glutamine) (Reference 1) supplemented with FGF2 (10 ng/mL) alone (STAGE 3).

After performing the differentiation of dermal papilla precursor cells from human induced pluripotent stem cells according to the above stages, changes in the morphology of cells were observed using a microscope and alkaline phosphatase (ALP) activity was measured in order to confirm whether the differentiation occurred well. As a result, as illustrated in FIG. 2C, it was observed that the cell shape was changed from a typical astral shape to a spindle and polygonal shape similar to human primary dermal papilla cells, and the proliferated dermal papilla precursor cells were isolated and it was confirmed that the isolated cells formed naturally three-dimensional spheres, which are the important intrinsic characteristic of dermal papilla cells.

Example 4. Production of Human Induced Pluripotent Stem Cell-Derived Dermal Papilla Precursor Cells (hiPSC-Derived DPPCs) in Hair Follicle Placode Stage The inventors of the present invention performed flow cytometry on each stage during a process of differentiating dermal papilla precursor cells from the human induced pluripotent stem cells of Example 3 and FIG. 2A to observe temporary changes in expression levels of SDC1 and CD133. As a result, as illustrated in FIG. 3A, it was confirmed that SDC1 expression was gradually increased as differentiation into dermal papilla precursor cells proceeded, whereas the expression of a stem cell marker CD133 was reduced. From the above results, it can be seen that, to obtain the SDC1+/CD133- cell population, day 25 to day 40 after differentiation started is a specific period at which the percentage of the cells reached a peak, i.e., 99%. Consistent with the above results, the pluripotent stem cell (SSEA3+) population was also gradually decreased during the differentiation process.

In addition to the above results, the inventors of the present invention attempted to analyze transient gene expression profiles in the cells (iPSC, NCSC, DPPC D25, DPPC D40, DPPC P5) of each differentiation stage. To this end, about 7 days after differentiation induction, the step-by-step progression of differentiation from induced pluripotent stem cells (iPSCs) (OCT3/4 and NANOG were expressed) into neural crest stem cells (NCSCs) (p75NTR, HNK11, and SOX10 were expressed) into dermal papilla precursor cells (DPPCs) (SDC1, biglycan [BGN], WNT5A, BMP4, and Hes-related family BHLH transcription factor [HEY1] having YRPW motif 1) was examined. As a result, as illustrated in FIG. 3B, it was confirmed that the expression of dermal papilla signature genes was increased from about 25 days after differentiation and the greatest expression levels were shown on day 40, and the expression levels were reduced according to subsequent passages similar to in-vitro cultured human dermal papilla cells. This expression pattern is consistent with SDC1 expression by flow cytometry.

Meanwhile, CD133 is known as a surface marker of hair-induced skin cells in mice. Therefore, the inventors of the present invention attempted to isolate CD133+ and CD133 cells from dermal papilla precursor cells on differentiation day 25 using magnetic beads and analyze the characteristics thereof. As a result, as shown in FIG. 3C, the expression of genes expressed in typical dermal papilla, i.e., ALX homeobox3 (ALX3), catenin beta 1 (CTNNB1), SOX2, and lymphoid enhancer binding factor 1 (LEF1) was significantly increased in the CD133 cells. In contrast, it was confirmed that the above-described result was not shown in the CD133+ cells.

Example 5. Analysis of Characteristics and Hair Follicle-Forming Ability of Human Induced Pluripotent Stem Cell-Derived Dermal Papilla Precursor Cells (hiPSC-Derived DPPCs)

Figure 4A:
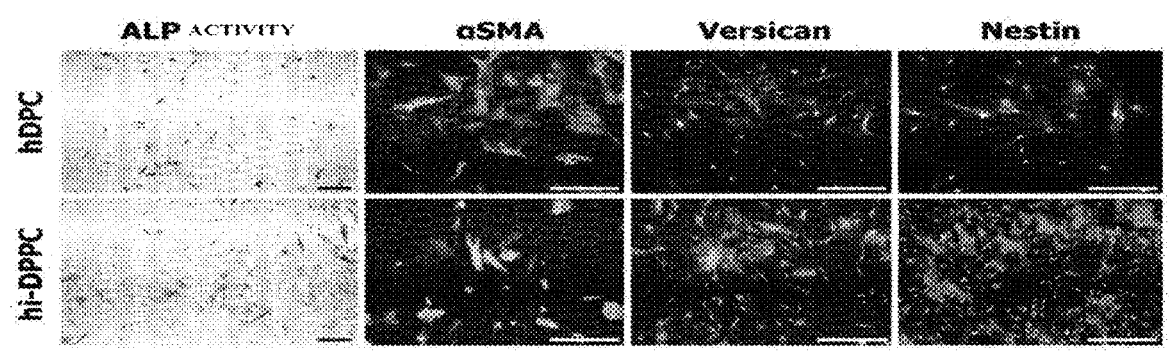

It was verified whether the dermal papilla precursor cells differentiated according to the method of Example 3 exhibited characteristics similar to those of human early dermal papilla cells (hDPCs). To this end, immunocytochemical staining was performed on human dermal papilla precursor cells (hi-DPPCs) to verify alkaline phosphatase (ALP) activity and the expression of genes, i.e., α-smooth muscle actin (αSMA), versican (VCAN), and nestin. As a result, as shown in FIG. 4A, alkaline phosphatase activity was observed even in dermal papilla precursor cells (hi-DPPCs) differentiated similar to human dermal papilla cells (hDPCs), and it was confirmed that αSMA, VCAN, and nestin were also strongly expressed.

Figure 4B:
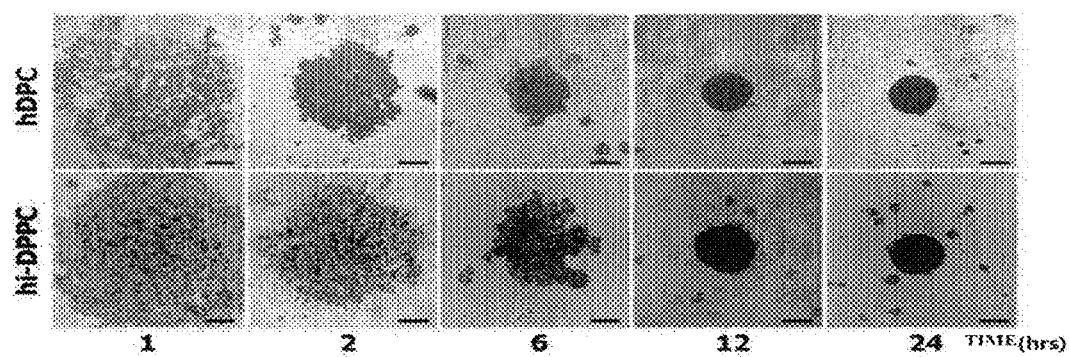

In addition, the spontaneous formation of spheres similar to the in-vivo structure of dermal papilla is an inherent characteristic of dermal papilla, which is related to hair-inducing potency and restoration of the intrinsic characteristics of human dermal papilla cells, and thus it was verified whether the dermal papilla precursor cells according to the present invention had a spherical shape. As a result, as illustrated in FIG. 4B, it was confirmed that dermal papilla precursor cells effectively formed a 3D spherical structure under very low attachment conditions which reflect the characteristics of human dermal papilla cells.

Figure 4C:
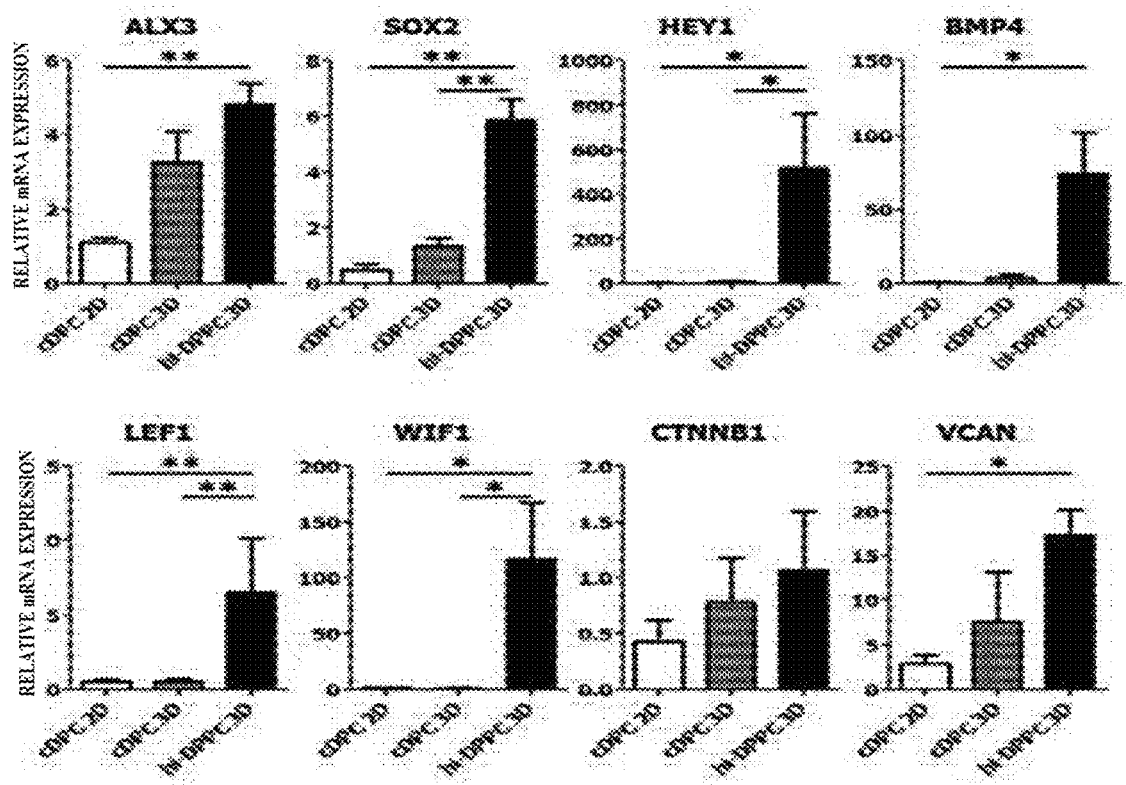

In addition, as a result of analyzing transcripts through quantitative PCR, as illustrated in FIG. 4C, it was confirmed that the expression of ALX3, SOX2, HEY1, BMP4, LEF1, WNT inhibitory factor 1 [WIF1], and VCAN, which are dermal papilla signature genes, was increased in human dermal papilla precursor cell spheres (hi-DPPC 3D) compared with human dermal papilla cells (cDPC 2D) and dermal papilla cell spheres (cDPC 3D). In particular, it can be seen that the expression of dermal papilla transcription factors was rapidly reduced in one-dimensional culture of dermal papilla cells, whereas the expression of ALX3, SOX2, and HEY1 was significantly increased in the hi-DPPC spheres compared with other cases. In addition, the expression of factors involved in WNT signaling pathways, including LEFT and WIF1 and factors involved in support matrix during hair follicle morphogenesis, such as VCAN was also significantly increased in the dermal papilla precursor cell spheres. These results indicate that dermal papilla precursor cells reflect the early precursor cell stage of human dermal papilla cells.

Furthermore, to determine whether the dermal papilla precursor cells according to the present invention are able to induce hair follicle formation when transplanted into severe combined immunodeficient hairless outbred (SHO) mice, the inventors of the present invention performed patch assay according to the method of Example 1-10. Specifically, human dermal papilla cell spheres (cDPD 3D) or dermal papilla precursor cell spheres (hiDPPC 3D) on differentiation day 40 were subcutaneously transplanted along with epithelial cells (mEPI) of C57BL/6 neonatal mice. Since the SHO mouse has no hair follicle and has an albino genetic background, it may be easy to distinguish black-colored hair follicles newly formed by C57BL/6 mouse-derived epithelial cells.

Figure 5A:
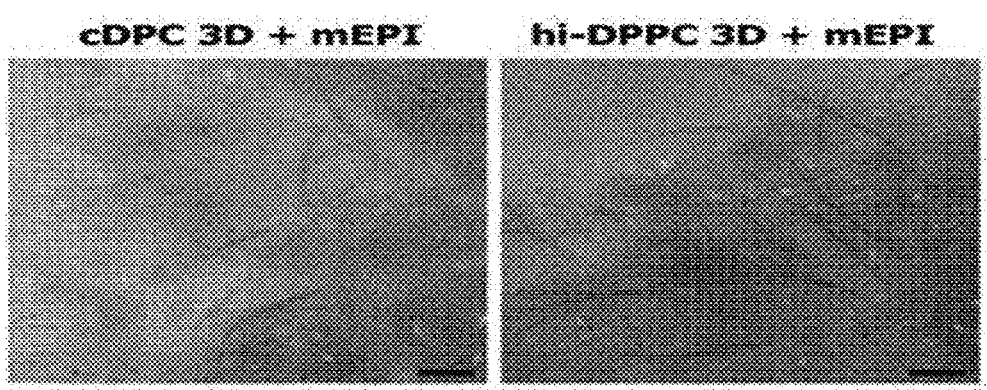
Figure 5B:
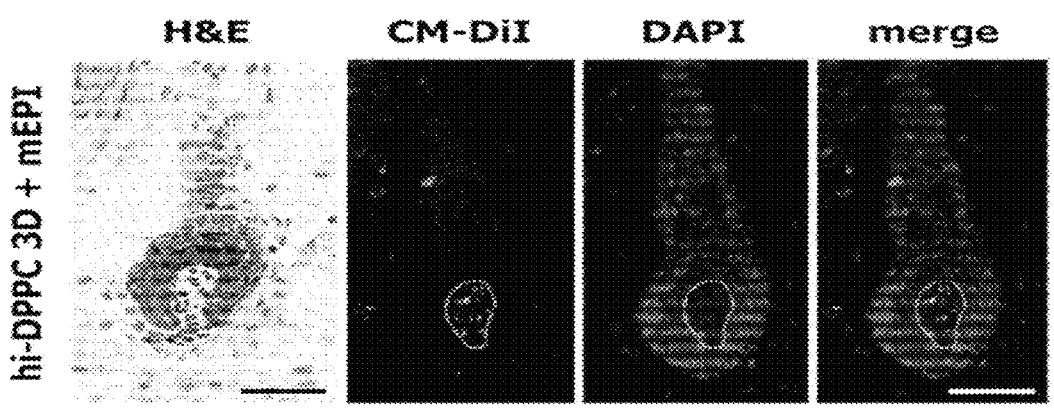

As a result, as illustrated in FIG. 5A, two weeks after experiment progression, a large number of new hybrid hair follicles was observed at a site where dermal papilla precursor cell spheres and dermal papilla cells were transplanted. In addition, as a result of labeling the dermal papilla precursor cells with red fluorescence cell tracer (CM-DiI) to determine whether the transplanted dermal papilla precursor cell spheres contribute to the dermal papilla of new hair follicles, as illustrated in FIG. 5B, red fluorescence was present in the dermal papilla of reconstructed hair follicles, from which it was confirmed that dermal papilla precursor cells were present and contributed to hair follicle neogenesis. In addition, the quantitative results of the hybrid hair follicle neogenesis are shown in Table 2 below.

TABLE 2

| Method | Dermal component | Epithelial component | Attempts | Hair follicle-forming ability | Newly formed structure |
|---|---|---|---|---|---|
| Patch assay | None | Neonatal mouse epithelial cells | 13 | 1/13 (0%) | Fibrotic cyst |
| | Dermal papilla precursor cells on day 40 | Neonatal mouse epithelial cells | 13 | 10/13 (76.92%) | Fibrotic cyst including newborn hair follicles |
| | Dermal papilla precursor cells after 5 passages | Neonatal mouse epithelial cells | 13 | 3/13 (23.07%) | Fibrotic cyst including newborn hair follicles |

Example 6. Gene Expression Profiling Analysis of Total RNA Isolated from Human Induced Pluripotent Stem Cell-Derived Dermal Papilla Precursor Cells (hiPSC-Derived DPPCs)

Figure 6A:
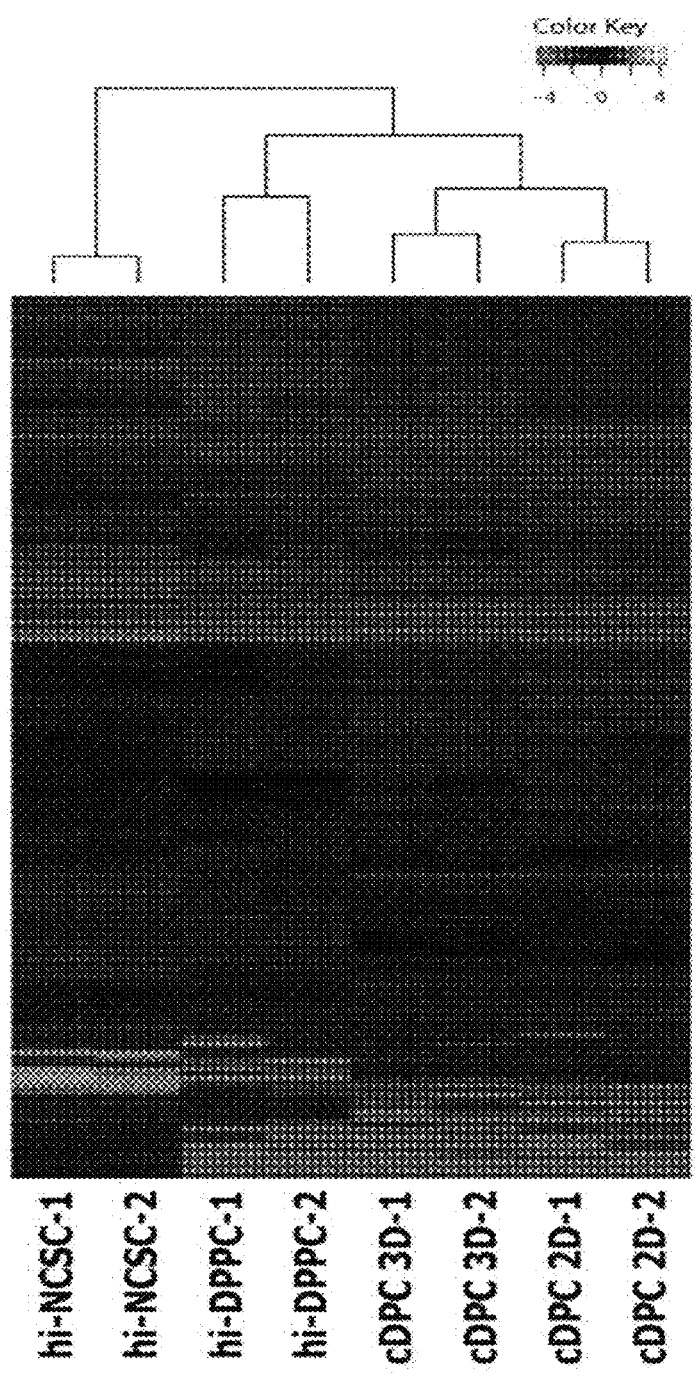
Figure 6B:
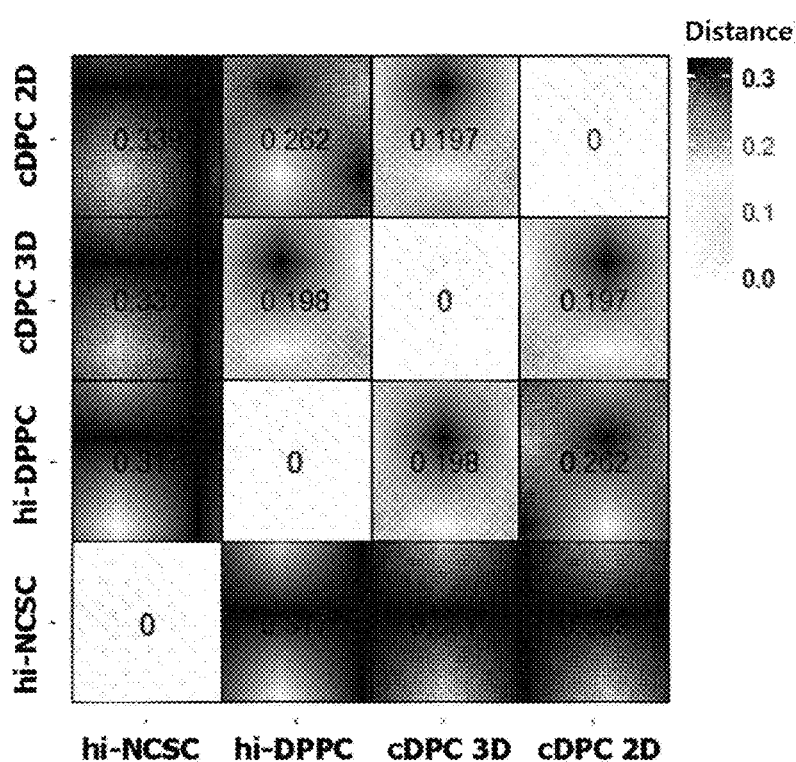
Figure 6C:
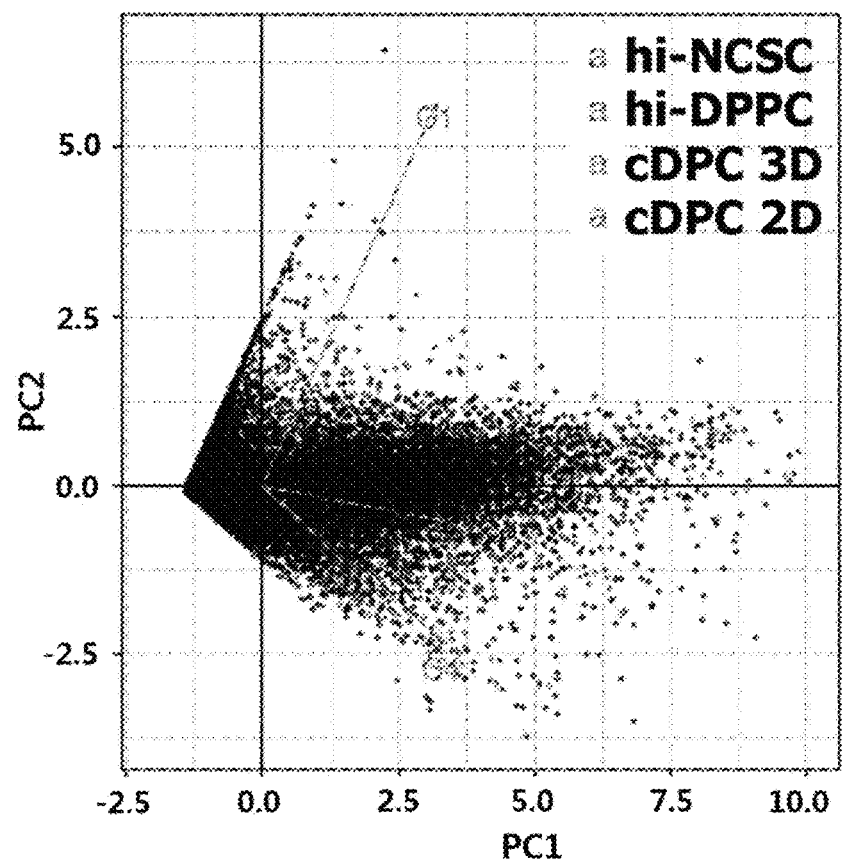

To confirm the gene expression profile of dermal papilla precursor cells according to the present invention, the inventors of the present invention performed RNA sequencing on human dermal papilla precursor cell spheres together with human induced pluripotent stem cell-derived neural crest stem cells (hi-NCSCs), human dermal papilla cell spheres (cDPC 3D), and human dermal papilla cells (cDPC 2D). As a result of generating a heatmap for a total of 3,065 genes and hierarchically clustering the same into a distance matrix, as illustrated in FIGS. 6A and 6B, the dermal papilla precursor cells were clustered with the dermal papilla cell spheres and the dermal papilla cells and exhibited a gene expression pattern very different from that of neural crest stem cells. In addition, as illustrated in FIG. 6C, based on the dimension reduction approach, the population of dermal papilla precursor cells was observed as an intermediate population distinguished in differentiation of dermal papilla cell spheres from neural crest stem cells.

Figure 6D:
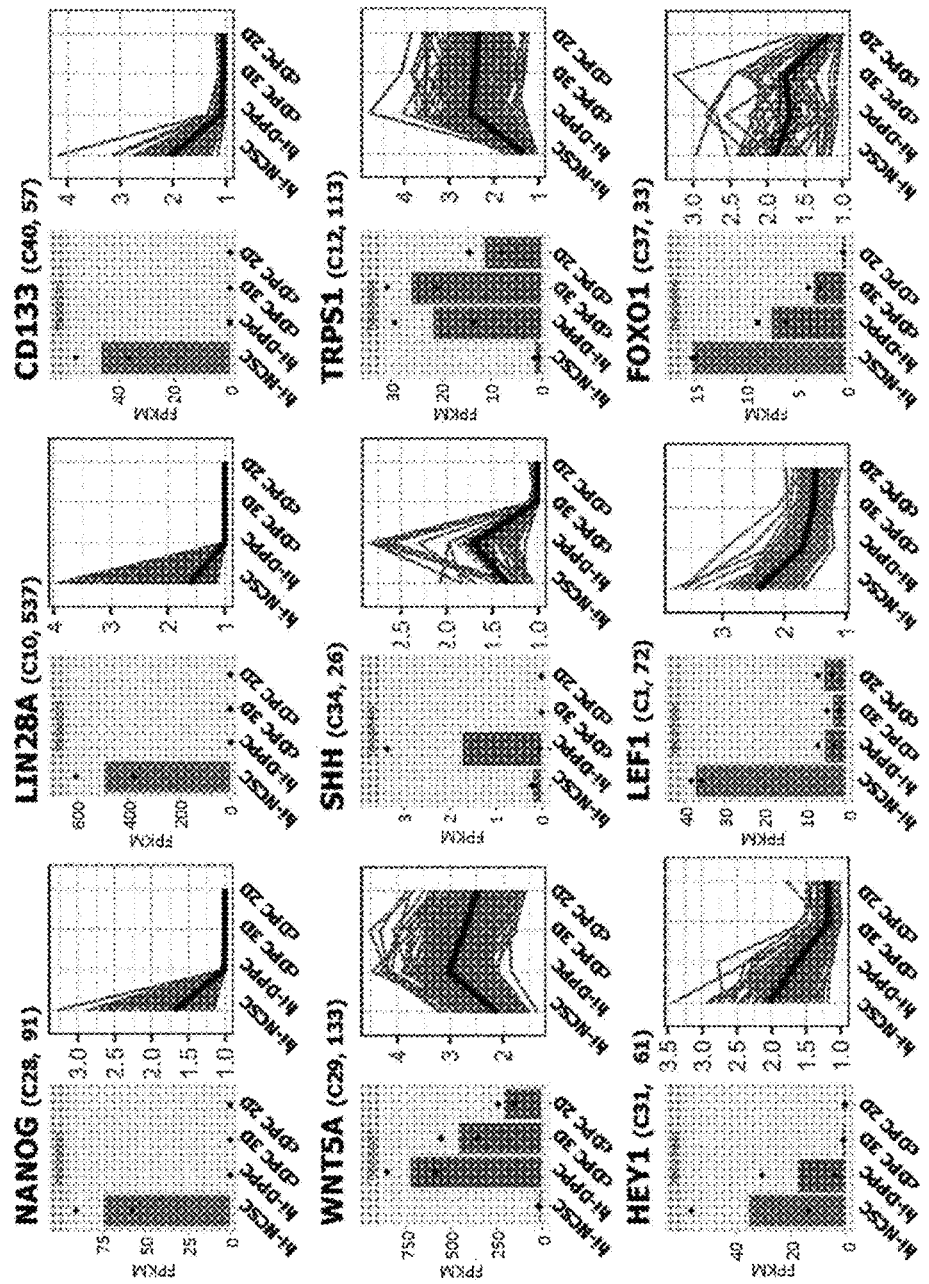

In particular, as a result of observing the expression of various genes, as illustrated in FIG. 6D, it was confirmed that many dermal papilla signature genes such as WNT5A, SHH, transcriptional repressor GATA binding 1(TRPS1), HEY1, LEF1, and FOXO1 were very highly expressed in the dermal papilla precursor cells compared to the dermal papilla cell spheres and the dermal papilla cells. In contrast, the expression of stem cell markers such as NANOG and LIN28A was barely found in the differentiated dermal papilla precursor cells. These results indicate that, contrary to neural crest stem cells before differentiation, the dermal papilla precursor cells are more similar to the human dermal papilla cell spheres than the dermal papilla cells or share a precursor molecular signature at the early stage.

Example 7. In-Vitro Formation of Human New Hair Follicels and Characterization Thereof To induce human hair follicle neogenesis in vitro, the inventors of the present invention induced differentiation of folliculogenic EpSCs from human induced pluripotent stem cells according to the known method of Example 1-4. Folliculogenic EpSCs (hi-EpSCs) differentiated according to the above method continuously expressed keratin 14 (K14), keratin 15 (K15), and integrin α6 on day 18 after differentiation induction, and induced hybrid hair follicles when bound to mouse neonatal skin cells (see FIG. 7B). Surprisingly, the human epithelial precursor cells expressed CD133 in the cell membrane together with β-catenin accumulation similar to in vivo epithelial placode cells at the hair follicle placode time.

Furthermore, to determine the hair follicle-forming ability of human dermal papilla precursor cells, the cells were cultured together with hi-EpSCs before analyzing in vivo hair follicle formation to perform in-vitro hair follicle formation analysis. First, dermal papilla precursor cells were dispensed onto a plate with very low adhesion at a density of 10,000 cells/well to form small spheres with their basement membranes containing recombinant human extracellular matrix proteins.

Figure 7A:
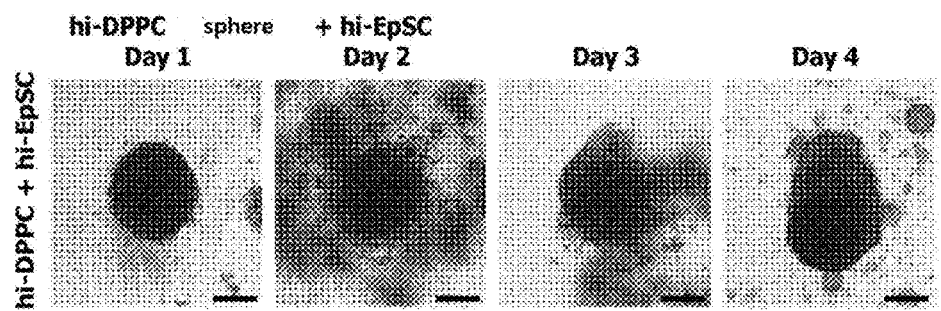

Next, the epithelial precursor cells were cocultured, at a density of 25,000 cells/well, with dermal papilla precursor cell spheres. As a result of culture, as illustrated in FIG. 7A, surprisingly, spherical structures very similar to follicular morphogenesis showing flat polarity and proliferation in the surrounding layer were produced through the mixing of the two types of cells (yield: ~65%).

Figure 7B:
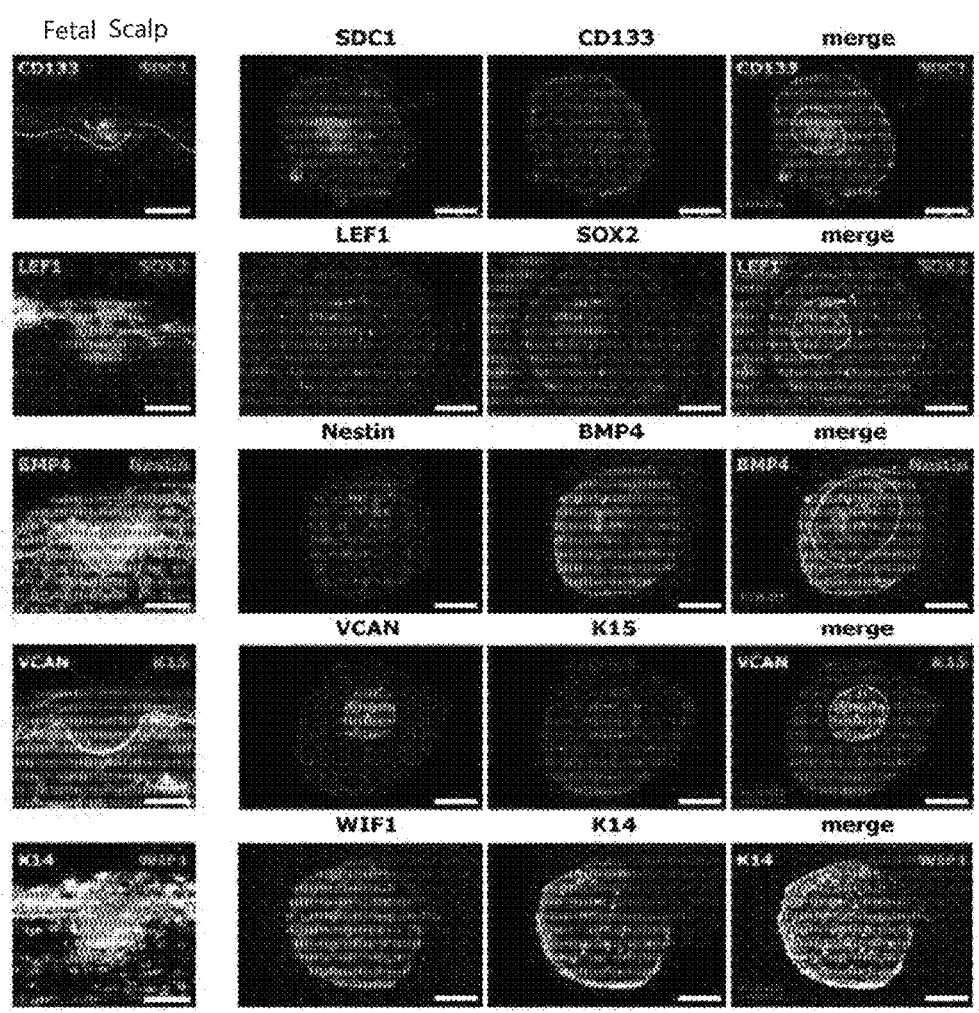

Next, the characteristics of skin and epithelial components were compared with the in vivo stage of the human fetal scalp. As a result, as illustrated in FIG. 7B, hair follicles exhibited expression patterns of skin markers (SDC1, LEF1, SOX2, Nestin, VCAN, and WIF1) and epithelial markers (CD133, BMP4, K15, K14, and WIF1) similar to the hair follicle placode stage. Interestingly, CD133 expression was shown to be slightly increased in skin components of cocultured hair follicles, similar to the hair germ or hair peg stage.

Example 8. Confirmation of Human Hair Follicle Neogenesis by Human Induced Pluripotent Stem Cell-Derived Dermal Papilla Precursor Cells (iPSC-Derived DPPCs) and Human Induced Pluripotent Stem Cell-Derived Epithelial Stem Cells (hiPSC-Derived EpSCs)

In the present invention, human hair follicle neogenesis was determined in mice using dermal papilla precursor cells differentiated from human induced pluripotent stem cells and epithelial stem cells. To this end, in vivo hair follicle neogenesis analysis was performed through chamber assay according to the method of Example 1-11, and dermal papilla precursor cell spheres (hi-DPPC D25, hi-DPPC D40, and hi-DPPC P25) at different times were transplanted together with epithelial stem cells (hi-EpSC D18) on day 18 after differentiation started, followed by histological analysis.

Figure 8A:
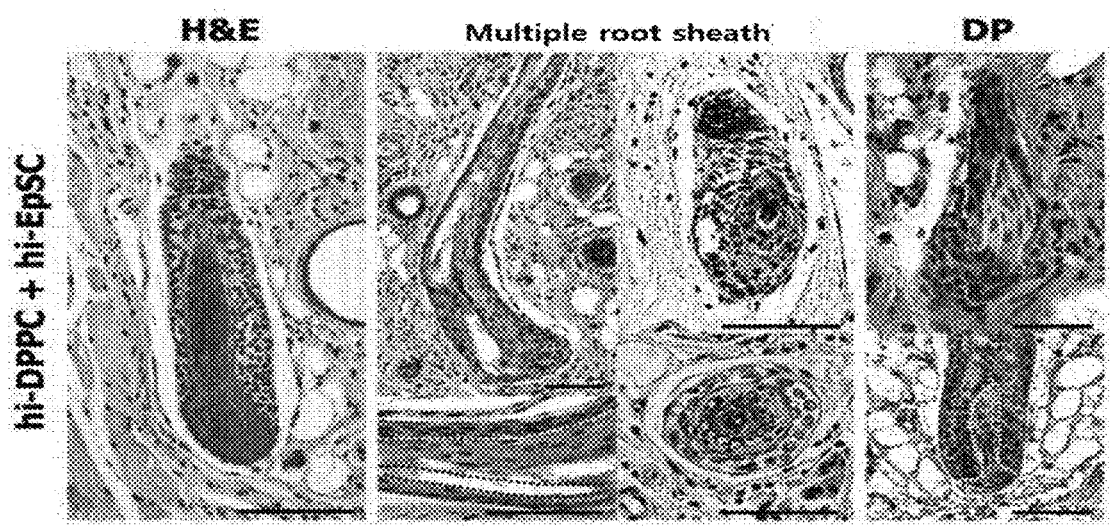
FIGS. 8A to 8C illustrate chamber assay results showing hair follicle neogenesis according to the transplantation of dermal papilla precursor cells differentiated from human induced pluripotent stem cells (hi-DPPC) and epithelial stem cells (hi-EpSC) in the body of mice.

As a result, it was observed as illustrated in FIG. 8A that a new hair follicle having multiple layers of epidermis, a dermal papilla structure, and a non-pigment hair shaft was formed. It was confirmed that the hair follicle exhibited a structure similar to that of human fetal scalp and was clearly different from the hair follicle with an incomplete structure produced in SHO mice.

Figure 8B:
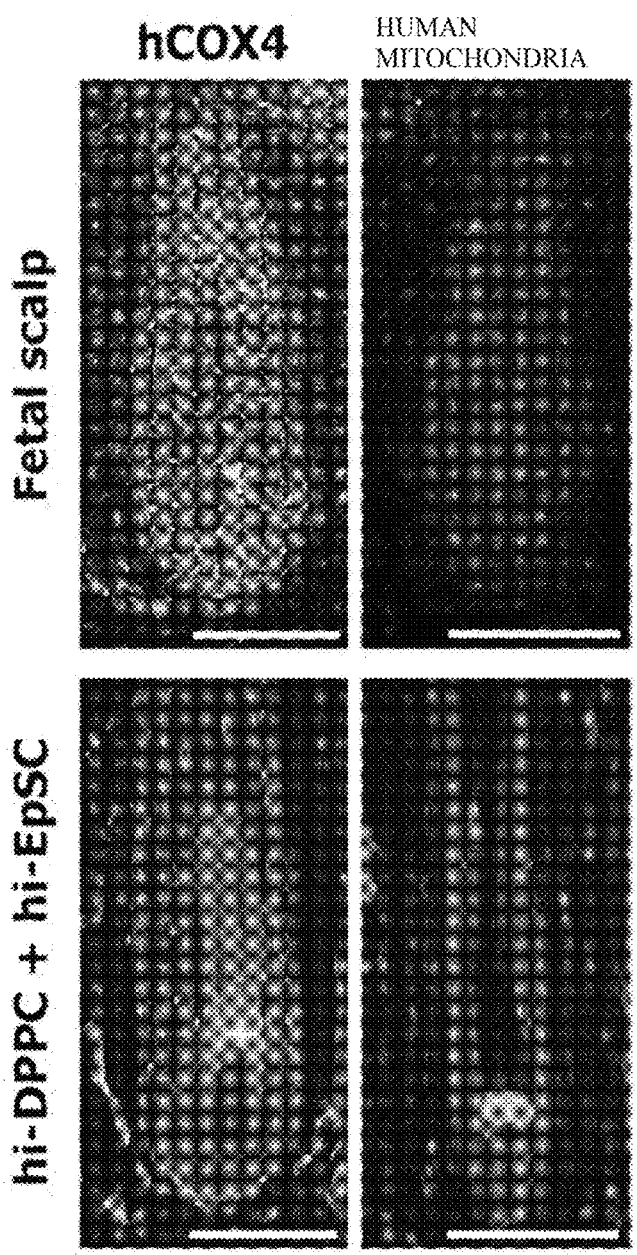
Figure 8C:
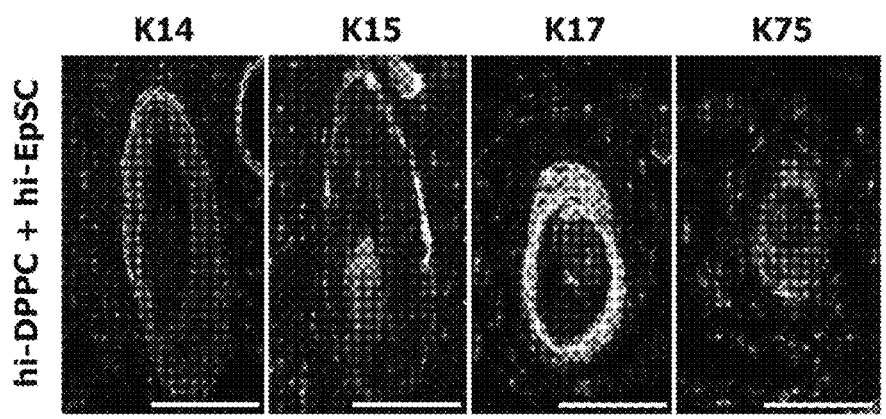

It was also confirmed as illustrated in FIG. 8B that, interestingly, the produced human hair follicle (hi-DPPC+ hi-EpSC) was positively stained by anti-human cytochrome c oxidase subunit 4 (COX4) antibody and an anti-human mitochondria antibody in the cytoplasm, similar to the human fetal scalp.

Furthermore, the multilayered expression of hair-specific keratin markers (K14, K15, K17, and K75) were observed in the central circle of newly formed hair follicle. K14 represents the outer root sheath, K15 represents hair follicle stem cells, K17 represents the hair medulla and hair follicle matrix, and K75 reflects the presence of a companion layer in the new hair follicle. In addition, the quantitative results of hair follicle neogenesis through the chamber assay are shown in Table 3 below, and it can be seen that, when dermal papilla precursor cells on differentiation day 40 and epithelial stem cells on differentiation day 18 were co-transplanted, hair follicle neogenesis efficiency is very high.

TABLE 3

| Dermal component | Epithelial component | Attempts | Hair follicle-forming ability | Newly formed structure |
| --- | --- | --- | --- | --- |
| None | Epithelial stem cells on day 18 | 2 | 0/2 (0%) | None |
| Dermal papilla precursor cells on day 40 | None | 2 | 0/2 (0%) | None |
| Dermal papilla precursor cells on day 25 | Epithelial stem cells on day 18 | 2 | 0/2 (0%) | None |
| Dermal papilla precursor cells on day 40 | Epithelial stem cells on day 18 | 6 | 5/6 (83.33%) | New hair follicle having multiple layers of epidermis, dermal papilla structure, and non-pigment hair shaft |

Through the above results, it was confirmed that human hair follicle neogenesis could be induced in mice using both dermal papilla precursor cells differentiated from the human induced pluripotent stem cells and epithelial precursor cells.

The foregoing description of the present invention is provided for illustrative purposes only, and it will be understood by those of ordinary skill in the art to which the present disclosure pertains that the present invention may be easily modified in other particular forms without changing the technical spirit or essential characteristics of the present invention. Thus, the above-described embodiments should be construed as being provided for illustrative purposes only and not for purposes of limitation.

The invention claimed is:

1. A method of differentiating SDC1$^+$ and CD133$^-$ dermal papilla precursor cells from human pluripotent stem cells, the method comprising the following processes:
   (a) culturing embryonic bodies of human pluripotent stem cells in a neural crest stem cell induction medium to differentiate into neural crest stem cells; and
   (b) culturing the differentiated neural crest stem cells in a medium composition for differentiation to differentiate into SDC1$^+$ and CD133$^-$ dermal papilla precursor cells;
   wherein the medium composition for differentiation comprises fibroblast growth factor-2 (FGF2), a glycogen synthase kinase-3 (GSK-3) inhibitor, and bone morphogenetic protein 4 (BMP4) in Dulbecco's Modified Eagle's Medium/Nutrient Mixture F-12 (DMEM/F12) L-alanyl-L-glutamine medium.

2. The method of claim 1, further comprising the following process:
   (c) aging the differentiated dermal papilla precursor cells to obtain dermal papilla precursor cells having a 3D spherical structure.

3. The method of claim 2, wherein process (c) is performed by culturing the differentiated dermal papilla precursor cells in DMEM/F12 L-alanyl-L-glutamine medium supplemented with FGF2 alone.

4. The method of claim 2, wherein process (c) is performed for 7 days to 13 days.

5. The method of claim 1, wherein the neural crest stem cell induction medium is DMEM/F12 L-alanyl-L-glutamine medium containing fibroblast growth factor-2 (FGF2), fibronectin, insulin, N$_2$ supplement, and transferrin.

6. The method of claim 1, wherein process (a) is performed for 5 days to 9 days, and process (b) is performed for 11 days to 17 days.

7. The method of claim 1, wherein the method of differentiating dermal papilla precursor cells from human pluripotent stem cells is performed for 26 days to 50 days.

8. The method of claim 1, wherein the dermal papilla precursor cells have hair follicle-forming ability.

9. The method of claim 8, wherein the dermal papilla precursor cells exhibit one or more characteristics selected from the group consisting of the following (a), (b), and (c):
   (a) positive immunological characteristics for alkaline phosphatase (ALP), α-smooth muscle actin (αSMA), versican (VCAN), and nestin;
   (b) structural properties of dermal papilla cells that spontaneously form spheres; and
   (c) genetic characteristics expressing one or more dermal papilla signature genes selected from the group consisting of ALX Homeobox 3 (ALX3), SRY-Box 2 (SOX2), Hes Related Family BHLH Transcription Factor With YRPW Motif 1 (HEY1), Bone Morphogenetic Protein 4 (BMP4), Lymphoid Enhancer Binding Factor 1 (LEF1), WNT inhibitory factor 1 (WIF1), and Versican (VCAN).

10. The method of claim 1, further comprising subculturing the dermal papilla precursor cells.

11. The method of claim 1, wherein the glycogen synthase kinase-3 (GSK-3) inhibitor comprises one or more selected from the group consisting of 6-bromoindirubin-3'-oxime (BIG), CHIR-99021, and SB-216763.

12. The method of claim 1, wherein the FGF2 is included at a concentration of 5 ng/ml to 30 ng/ml, the GSK-3 inhibitor is included at a concentration of 0.1 μM to 10 μM, and the BMP4 is included at a concentration of 0.5 ng/ml to 5 ng/ml.

13. The method of claim 11, wherein the BIO is included at a concentration of 0.5 μM to 5 μM, and the CHIR 99021 is included at a concentration of 0.1 μM to 10 μM.

14. The method of claim 1, wherein the human pluripotent stem cells are human embryonic stem cells or human induced pluripotent stem cells.

15. The method of claim 1, wherein the medium composition for differentiation does not incorporate human neonatal fetal tissue.

\* \* \* \* \*